US011471551B1

(12) United States Patent
Leavitt et al.

(10) Patent No.: US 11,471,551 B1
(45) Date of Patent: Oct. 18, 2022

(54) APPARATUS FOR INACTIVATION OF AIRBORNE PATHOGENS

(71) Applicant: MICRON PURE, LLC, Olathe, KS (US)

(72) Inventors: David D. Leavitt, Shawnee, KS (US); John R. Bergida, Wildwood, MO (US); Timothy B. Jackson, Maryland Heights, MO (US); Paul Helgemo, Chesterfield, MO (US); Devlin Leavitt, Lenexa, KS (US); Channary Ny, Kansas City, MO (US); Corey Boddicker, Overland Park, KS (US); Tony Bergida, Olathe, KS (US); Michael McMahon, Livingston, TX (US)

(73) Assignee: Micron Pure, LLC, Olathe, KS (US)

( * ) Notice: Subject to any disclaimer, the term of this patent is extended or adjusted under 35 U.S.C. 154(b) by 0 days.

(21) Appl. No.: 17/470,306

(22) Filed: Sep. 9, 2021

(51) Int. Cl.
   *B01D 53/00*   (2006.01)
   *A61L 9/12*    (2006.01)
   (Continued)

(52) U.S. Cl.
   CPC .......... *A61L 9/122* (2013.01); *B01D 46/0028* (2013.01); *B01D 46/0038* (2013.01); *B01D 53/047* (2013.01); *B01D 53/30* (2013.01); *B01D 53/8675* (2013.01); *B01J 19/006* (2013.01); *B01J 23/34* (2013.01); *B01J 35/04* (2013.01); *C01B 13/10* (2013.01); *A61L 2209/111* (2013.01); *A61L 2209/134* (2013.01);
   (Continued)

(58) Field of Classification Search
   CPC ..... A61L 9/122; A61L 9/015; B01D 46/0028; B01D 53/017; B01D 53/8675; C01B 13/10
   See application file for complete search history.

(56) References Cited

U.S. PATENT DOCUMENTS

| 4,343,765 A | 8/1982 | Elston et al. |
| 4,370,301 A | 1/1983 | Doi et al. |
| (Continued) | | |

FOREIGN PATENT DOCUMENTS

CN      109631195 A  *  4/2019  ............ F24F 13/28

OTHER PUBLICATIONS

U.S. Appl. No. 63/019,522, filed May 4, 2020, 31 pages.
U.S. Appl. No. 63/003,344, filed Apr. 1, 2020, 39 pages.
U.S. Appl. No. 62/944,397.

*Primary Examiner* — Robert A Hopkins
(74) *Attorney, Agent, or Firm* — Lathrop GPM LLP

(57) ABSTRACT

An apparatus and method for inactivation of airborne pathogens to include a reactor space with an intake opening, an exhaust opening, and an airflow path disposed between the intake and exhaust openings for air to continuously transit throughout the reactor space. The apparatus also includes at least one of (i) a corona discharge unit with a pressure swing adsorption unit, or (ii) a UV-C germicidal lamp to generate a sufficient concentration of ozone and UV light to inactive pathogens. The apparatus also includes a catalyst disposed within the path of the airflow to convert ozone to oxygen following the inactivation step and an adsorbent to remove nitrogen oxides from the air. The apparatus also includes sensors for measuring ozone and nitrogen oxides concentrations at the exhaust opening.

43 Claims, 20 Drawing Sheets

(51) Int. Cl.

| | | |
|---|---|---|
| *C01B 13/10* | (2006.01) | |
| *B01D 46/00* | (2022.01) | |
| *B01D 53/047* | (2006.01) | |
| *B01D 53/30* | (2006.01) | |
| *B01J 23/34* | (2006.01) | |
| *B01J 35/04* | (2006.01) | |
| *B01J 19/00* | (2006.01) | |
| *B01D 53/86* | (2006.01) | |

(52) U.S. Cl.
CPC ..... *A61L 2209/14* (2013.01); *A61L 2209/212* (2013.01); *B01D 2253/108* (2013.01); *B01D 2255/2073* (2013.01); *B01D 2255/9155* (2013.01); *B01D 2257/106* (2013.01); *B01D 2257/404* (2013.01); *B01D 2279/65* (2013.01)

(56) References Cited

U.S. PATENT DOCUMENTS

| | | | |
|---|---|---|---|
| 5,681,533 A * | 10/1997 | Hiromi | F24F 3/16 422/121 |
| 5,961,919 A | 10/1999 | Tachibana et al. | |
| 6,312,606 B1 | 11/2001 | Conrad | |
| 6,528,023 B2 | 3/2003 | Fleischer | |
| 6,537,484 B2 | 3/2003 | Nakagawa et al. | |
| 6,558,636 B2 | 5/2003 | Tamura et al. | |
| 6,589,486 B1 | 7/2003 | Spanton | |
| 6,605,260 B1 | 8/2003 | Busted | |
| 6,620,379 B1 | 9/2003 | Piuk et al. | |
| 6,620,380 B2 | 9/2003 | Thomas et al. | |
| 6,630,105 B1 | 10/2003 | O'Neill et al. | |
| 6,635,153 B1 | 10/2003 | Whitehead | |
| 6,652,816 B2 | 11/2003 | Hwang | |
| 6,680,033 B2 | 1/2004 | Ishii | |
| 6,682,707 B2 | 1/2004 | Chao | |
| 6,764,659 B2 | 7/2004 | Perlov et al. | |
| 6,793,897 B2 | 9/2004 | Shannon | |
| 6,824,693 B1 | 11/2004 | Sauska et al. | |
| 6,866,828 B2 | 3/2005 | Segawa et al. | |
| 6,872,366 B2 | 3/2005 | Thomas et al. | |
| 6,893,618 B2 | 5/2005 | Kotlyar | |
| 6,967,008 B1 | 11/2005 | Barnes | |
| 6,974,560 B2 | 12/2005 | Taylor et al. | |
| 6,984,361 B2 | 1/2006 | Carman et al. | |
| 6,991,768 B2 | 1/2006 | Keras et al. | |
| 7,098,462 B2 | 8/2006 | Chua et al. | |
| 7,121,079 B2 | 10/2006 | Calvo et al. | |
| 7,250,145 B1 | 7/2007 | Miller et al. | |
| 7,326,387 B2 | 2/2008 | Arts et al. | |
| 7,407,624 B2 | 8/2008 | Cumberland et al. | |
| 7,407,633 B2 | 8/2008 | Potember et al. | |
| 7,438,870 B2 | 10/2008 | Anno | |
| 7,588,720 B2 | 9/2009 | Turcot et al. | |
| 7,604,774 B2 | 10/2009 | Mole et al. | |
| 7,604,780 B2 | 10/2009 | Teran et al. | |
| 7,608,217 B2 | 10/2009 | Champagne | |
| 7,901,618 B2 | 3/2011 | McVey et al. | |
| 7,943,098 B2 | 5/2011 | Phillips et al. | |
| 8,038,936 B2 | 10/2011 | Sim et al. | |
| 8,105,546 B2 | 1/2012 | Lanz | |
| 8,128,869 B2 | 3/2012 | Sunderland | |
| 8,211,208 B2 | 7/2012 | Chan et al. | |
| 8,211,374 B2 | 7/2012 | Hallam | |
| 8,221,678 B2 | 7/2012 | Hedman | |
| 8,236,236 B2 | 8/2012 | Garner | |
| 8,241,563 B2 | 8/2012 | Kolve et al. | |
| 8,318,084 B2 | 11/2012 | Johnson et al. | |
| 8,329,096 B2 | 12/2012 | Elrod et al. | |
| 8,337,759 B1 | 12/2012 | Alford et al. | |
| 8,354,057 B2 | 1/2013 | Heselton | |
| 8,357,331 B2 | 1/2013 | McVey et al. | |
| 8,361,402 B2 | 1/2013 | Tsui | |
| 8,367,010 B2 | 2/2013 | Chen et al. | |
| 8,388,900 B2 | 3/2013 | Benedek et al. | |
| 8,549,994 B2 | 10/2013 | Mole | |
| 8,627,531 B2 | 1/2014 | Ninomiya et al. | |
| 8,667,817 B2 | 3/2014 | Smith et al. | |
| 8,747,763 B2 | 6/2014 | Tandou et al. | |
| 8,758,679 B2 | 6/2014 | Hyde et al. | |
| 8,845,782 B2 | 9/2014 | Metteer | |
| 8,865,065 B2 | 10/2014 | Kain et al. | |
| 8,992,837 B2 | 3/2015 | Jung et al. | |
| 9,034,249 B2 | 5/2015 | Foreman et al. | |
| 9,119,892 B2 | 9/2015 | Mueller et al. | |
| 9,205,166 B2 | 12/2015 | Segura Rius et al. | |
| 9,216,233 B2 | 12/2015 | Ota et al. | |
| 9,233,183 B2 | 1/2016 | Kim | |
| 9,474,822 B2 | 10/2016 | Jung et al. | |
| 9,509,125 B2 | 11/2016 | Waddell et al. | |
| 9,610,559 B2 | 4/2017 | Riskin et al. | |
| 9,711,317 B2 | 7/2017 | Weibel et al. | |
| 9,987,388 B2 | 6/2018 | Jurak et al. | |
| 10,010,644 B2 | 7/2018 | Burnett | |
| 10,143,763 B2 | 12/2018 | Campalans | |
| 10,265,432 B2 | 4/2019 | Paranhos et al. | |
| 10,281,168 B2 | 5/2019 | Meirav et al. | |
| 10,363,522 B2 | 7/2019 | Bender et al. | |
| 10,386,080 B2 | 8/2019 | Lee et al. | |
| 10,478,517 B2 | 11/2019 | Hauville et al. | |
| 10,581,227 B2 | 3/2020 | Haruna et al. | |
| 10,583,213 B2 | 3/2020 | Stibich et al. | |
| 10,675,375 B2 | 6/2020 | Jiang | |
| 10,729,801 B2 | 8/2020 | Woodbridge | |
| 10,739,023 B2 | 8/2020 | Buske et al. | |
| 10,933,158 B2 * | 3/2021 | Benedek | B01D 53/869 |
| 10,988,270 B2 | 4/2021 | Gorbatenko et al. | |
| 2004/0262241 A1 * | 12/2004 | Socha | A61L 9/015 422/4 |
| 2008/0175671 A1 * | 7/2008 | Bowman | B09C 1/002 405/128.5 |
| 2015/0297771 A1 * | 10/2015 | Law | A61L 9/00 423/210 |

\* cited by examiner

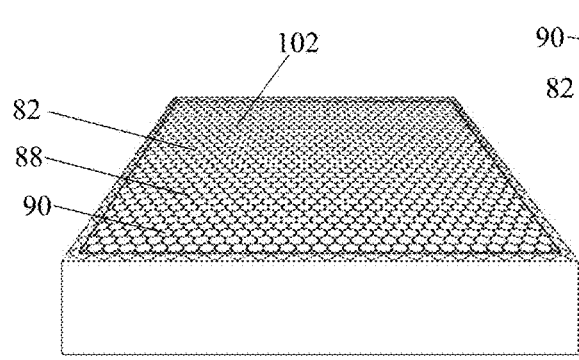 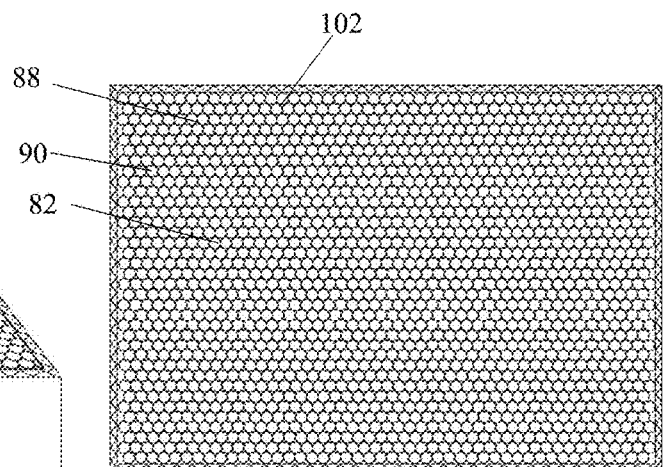
FIG. 16A                FIG. 16B
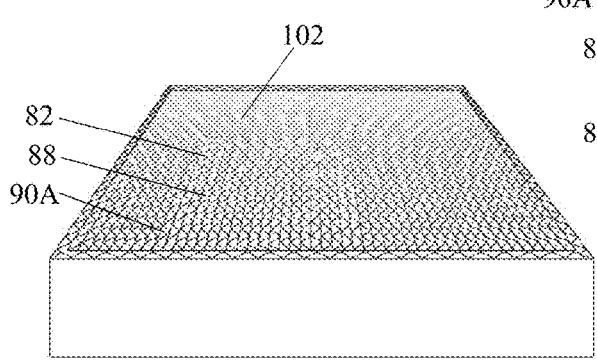 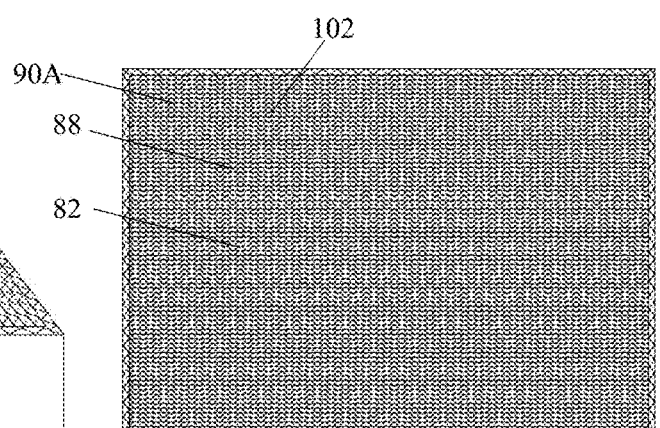
FIG. 17A                FIG. 17B

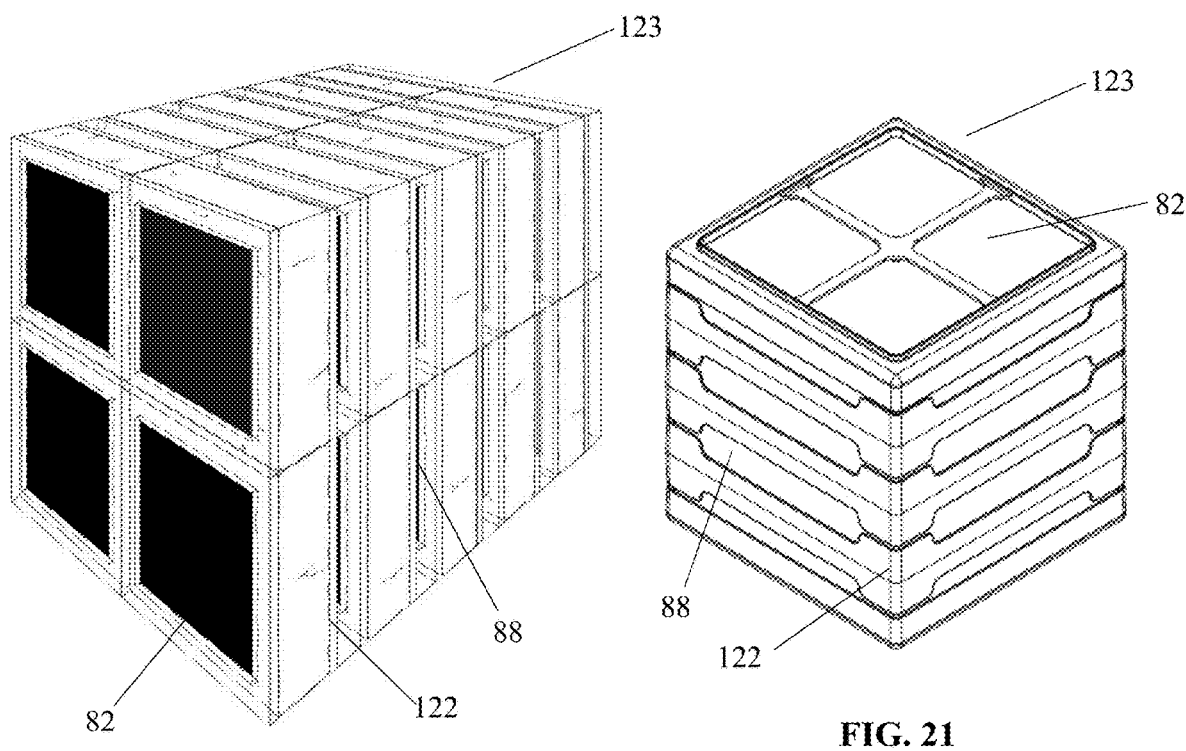
FIG. 20
FIG. 21
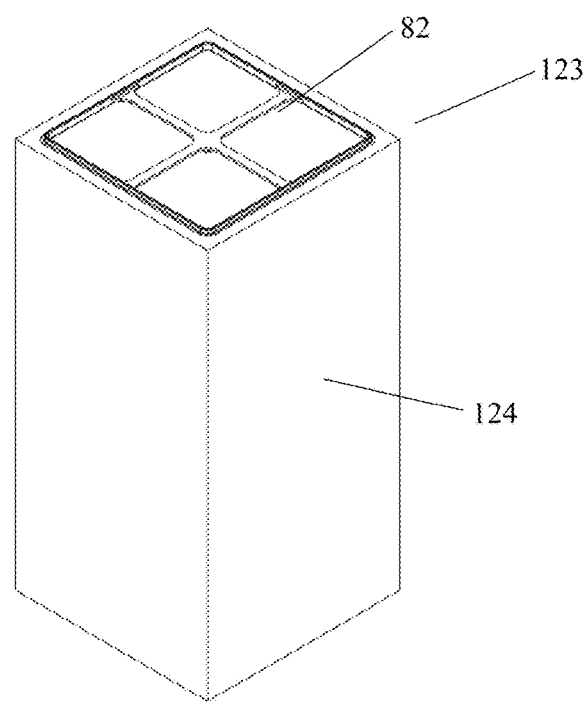
FIG. 22

ABSTRACT

APPARATUS FOR INACTIVATION OF AIRBORNE PATHOGENS

FIELD OF USE

This disclosure is directed to an apparatus and method for inactivating airborne pathogens such as viruses, bacteria, and fungal spores with ozone followed by catalytic decomposition of the generated ozone.

BACKGROUND

Many diseases are transmitted from exposure to airborne pathogens such as viruses and bacteria. These organisms may be spread through sneezing, coughing, spraying of liquids, the spread of dust, or any activity that results in the generation of aerosolized particles. These aerosolized particles may be generated from a source of infection, such as body secretions from an infected patient or animal, flushing of a toilet with the lid open, or from biological waste products that accumulate in garbage, caves, and various other containers.

Once the droplets containing the pathogens have been formed, they are then dispersed via air currents and can be inhaled by susceptible hosts. The aerosolized particles may remain suspended in air for hours and can travel considerable distances. Proper precautions must be taken to mitigate the risk of infection in public places such as hospitals or private places like homes. The airborne particles may remain localized to a single room or may move to other rooms depending on the airflow.

In cases where there is inadequate ventilation, airborne particles may remain in the building or room and be inhaled by one or more occupants. To control and prevent the airborne transmission of pathogens, many methods are implemented, such as air purifiers, the practice of antiseptic techniques, wearing personalized protection equipment (PPE), and performing basic infection prevention measures like hand washing. Airborne diseases are caused by pathogenic microbes small enough to be discharged from an infected person via coughing, sneezing, laughing, and other close personal contact. The discharged microbes remain suspended in air on dust particles or water droplets.

Inhalation exposes the upper and lower respiratory tracts of humans to a variety of airborne particles and vapors. Airborne transmission of pathogenic microorganisms to humans from the environment, animals, or other humans can result in disease. Inhalation is an important route of exposure as the lung is more susceptible to infection than the gastrointestinal tract.

Ingested microorganisms must pass through the acidic environment of the stomach before they can colonize tissue while inhaled microorganisms are deposited directly on the moist surfaces of the respiratory tract. Inhalation of microbial aerosols can elicit adverse human health effects including infection, allergic reaction, inflammation, and respiratory disease. Following inhalation, infectious viruses, bacteria, and fungi can establish in host cells of the respiratory tract. Some are translocated and infect the gastrointestinal tract and other tissues.

Airborne diseases such as the common cold are typically caused by viruses such as rhinoviruses. Rhinoviruses can often change strain allowing for easier infection of humans. Another virus, varicella zoster, causes chickenpox and spreads easily among young children; The virus mumps affects the glands just below the ears, causing swelling and, in some cases, loss of hearing. The bacteria *Bordetella pertussis* causes the illness called whooping cough which leads to swelling of the airway. Additionally, a rapidly spreading coronavirus, SARS-CoV-2, and the disease it causes, COVID-19, continue to cause worldwide challenges. The most common symptoms of COVID-19 include fever, cough, fatigue, and shortness of breath.

To inactivate pathogens, oxidants such as ozone and hydroxyl radicals have been proposed as alternatives to traditional disinfectant compounds such as chlorinated bleach or hydrogen peroxide. Ozone is capable of being generated from air at the site of disinfection, eliminating the need to store liquid disinfectants. Ozone molecules target the DNA or RNA of viruses and bacteria, damaging the chemical structure and resulting in pathogen inactivation. In the apparatus as disclosed herein, ozone is generated within a reactor to inactivate pathogens within an airstream. The ozone is then removed along with any additional by-products formed to ensure safe release of the airstream into an environment. The apparatus operates continuously and is scalable to handle high flow rates for larger spaces as well as low flow rates for smaller spaces that may result in a smaller reactor configuration.

SUMMARY

There exists a tremendous need for an apparatus or system to inactivate or attenuate airborne pathogens such as viruses. To inactivate or attenuate a pathogen means to cause the pathogen to lose disease producing capacity. To render a very high percentage, if not all airborne pathogens inactive, is the ultimate objective of the apparatus disclosed herein. To inactivate pathogens, ozone is generated within a reactor and mixed in an airstream. As air flows through the reactor, ozone is mixed in the airstream, contacting and inactivating airborne pathogens. Before the newly disinfected airstream can be released into the atmosphere, ozone and other by-products are removed, as ozone can cause lung irritation if inhaled. After these processes are completed, the airstream is then released back to the environment.

The apparatus, in a first embodiment as disclosed herein, is configured for placement into an enclosed space, such as a room within a private residence, a movie theater, a warehouse, a fulfillment center, a cabin of an aircraft, public transit buses, and trains. The inactivation of pathogens is critical to avoid infection of the occupants by the pathogen, where air is aspirated by human beings often in constrained spaces. In an alternative embodiment, it is also contemplated by this disclosure to develop a personal, and portable, airborne pathogen inactivation apparatus that allows a user to carry the device with them to include an appropriately configured apparatus to support breathing of the air exiting the apparatus following inactivation of the pathogens.

The apparatus, as disclosed herein, may be sized to accommodate smaller venues such as a residence or a much larger venue such as a warehouse. The apparatus may be appropriately sized to cycle through the entire volume of air contained within the structure in a set amount of time known as the clean air delivery rate (CADR). Ideally the apparatus, depending upon initial design criteria, can be manually transported to another location in the structure, such as another room of a residence should the occupant intend to spend more time in a specific room.

The disclosed device comprises a chamber or a reactor into which air is inducted with a fan through an intake opening. The intake air is pre-filtered upon entering the chamber. The objective of the pre-filter is to remove some portion of the airborne particulates; however, the preferred filter efficiency is such that it does not restrict airflow into the reactor. In other words, the preferred pre-filter would be classified as those filters known as MERV filters. MERV stands for "medium efficiency reporting value," a rating for the capability of a filter to remove particles as large as 10 microns and smaller than 1 micron. The pre-filter would have a MERV rating in the range of 7-16, capable of removing particulates from 3 to 0.3 microns in size such as dust, oils, powders, and various larger pathogens.

The preferred embodiment of the apparatus as disclosed herein also utilizes a backflow preventer to reduce, or preferably eliminate, the potential for air leakage out of the reactor space via the intake opening, as the air may contain ozone that has not been converted to oxygen. The backflow preventer may be as basic as a hinged flapper or semi-flexible panel that stops the airflow moving through the intake area. In an alternative embodiment, an ozone decomposition catalyst located proximate the intake opening of the reactor can also provide the function of a backflow preventer such that when the intake fan to the unit is turned off, any ozone present in the air moving back out through the catalyst will be converted into oxygen before exiting through the pre-filter. The preferred embodiment utilizes manganese dioxide ($MnO_2$) coated on a honeycomb monolithic substrate. The monolithic substrate will typically be a ceramic such as cordierite or a metal compound.

The next component within the reactor space is a fan that serves to draw air in through the intake opening of the reactor and to move it forward into the reactor space. Because the fan rotates at a high rate of speed there are frictional forces that result between the fan blades and the air that results in a build-up of static electricity. This static electricity causes dust particles to adhere to the edges of the fan blades and to reduce efficiency of the fan. The previously detailed pre-filter serves to reduce the potential for admission of dust particles that can adhere to the fan blades and other interior chamber surfaces.

A variable speed fan is also contemplated by this disclosure to address the need for increased throughput of the apparatus or reducing throughput to decrease the sound generated by the movement of air through the device when a quieter setting may be required. In various embodiments, the fan may be located (i) before the backflow preventer or first ozone decomposition catalyst, (ii) after the backflow preventer or first ozone decomposition catalyst, or (iii) proximate the exhaust opening of the apparatus disclosed herein.

Adjacent to the fan is the ozone generating device. Various embodiments of the ozone generation source are contemplated by this disclosure. A first embodiment utilizes solely a corona discharge device. In a corona discharge device, a voltage is applied between two electrodes, causing air between the electrodes to be ionized. This ionization splits diatomic oxygen, producing an atomic oxygen molecule that reacts to form ozone. Common variants of corona discharge devices include dielectric barrier discharge, non-thermal plasma, and ionic wind. It is contemplated by this disclosure that the concentration of ozone within the apparatus would be between 1 and 55 parts per million (PPM).

An undesirable by-product of the production of ozone from corona discharge in ambient air is the formation of nitrogen oxides ($NO_x$) including nitrogen dioxide ($NO_2$), nitrogen oxide (NO) and dinitrogen pentoxide ($N_2O_5$). These nitrogen oxides are created from corona discharge because dry air is rich in diatomic nitrogen, composed of 78% by volume. When air enters the corona discharge device, diatomic nitrogen is split in the same manner as diatomic oxygen, creating atomic nitrogen which can react with oxygen or ozone to form nitrogen oxides.

At higher concentrations of produced ozone from corona discharge, the predominant nitrogen oxide is nitrogen dioxide ($NO_2$). This is because ozone will oxidize other nitrogen oxides like NO to $NO_2$. The National Ambient Air Quality Standards established by the U.S. Environmental Protection Agency and codified at 40 CFR § 50.11 set a one-hour maximum nitrogen dioxide concentration of 100 parts per billion (PPB) and an average annual concentration of 53 parts per billion. The objective of the corona discharge device, as previously discussed, is to generate ozone at a sufficiently high concentration and with a residence time sufficient to inactivate airborne pathogens. The nitrogen oxides by-products are undesirable and are preferably removed from the airflow prior to reaching the exhaust opening of the apparatus disclosed herein.

Avoidance of the production of nitrogen dioxide and associated compounds is a preferable path and an embodiment to accomplish such an end is also disclosed. A well-established technology known as "pressure swing adsorption" (PSA), may be employed. Pressure swing adsorption is commonly used in oxygen concentrators to separate nitrogen from oxygen. This process is used to reduce the concentration of nitrogen available for formation of nitrogen oxides in the reactor space.

In a preferred embodiment for use within the reactor disclosed herein, the pressure swing adsorption equipment utilizes two vessels (tanks) that are capable of withstanding internal gas pressures of up to about 150 psi and preferably higher in some instances. While the first vessel is being pressurized the second vessel is depressurized, hence the reason for the use of the term "swing" in the name of the identified technology. Within each vessel, an adsorbent is used that has a high affinity for nitrogen, but not for oxygen, when pressurized. Aluminosilicate compounds called zeolites are among the most commonly used adsorbents in pressure swing adsorption for oxygen concentration.

In the first vessel, nitrogen is adsorbed by the zeolite which is positioned in the form of a bed at the base of the vessel, allowing a concentrated oxygen stream to pass through the bed and out the top. This concentrated oxygen stream can then be routed out of the top of the pressurized vessel and into the corona discharge device, reducing the formation of significant concentrations of nitrogen oxides, i.e., $NO_2$, NO, $N_2O_5$, etc., and substantially increasing the concentration of ozone to levels between 1,000 and 60,000 parts per million produced within the corona discharge device. Once the zeolite has reached its maximum adsorption capacity for nitrogen, the first vessel must be regenerated to allow for further nitrogen adsorption. To do this, the inlet airstream is routed to the second vessel to ensure continuous operation while the first vessel is regenerated.

To regenerate the first vessel, the vessel is depressurized, causing the nitrogen to desorb from the surface of the zeolite. This desorbed stream containing concentrated nitrogen can then be safely released into the ambient atmosphere surrounding the pressure swing adsorption vessels without harm to human health because nitrogen does not cause pulmonary distress as do nitrogen oxides. The process is completed again for the second vessel once the maximum nitrogen adsorption capacity is reached, switching the inlet airstream to the newly regenerated first vessel to maintain constant oxygen production. Typically, the oxygen concentration leaving a pressure swing adsorption oxygen concentrator is greater than 90%, but not more than 99%. Some pressure swing adsorption units can generate oxygen at lower concentrations, such as 50% purity.

It is contemplated by this disclosure in at least one embodiment that a portion of the overall airstream passing through the corona discharge device is the oxygen continuously routed from the vessels of the pressure swing adsorption unit. Some nitrogen will be present in the airstream entering the corona discharge device, allowing for minimal creation of nitrogen oxides that will stay below the safe maximum concentration limit set by the U.S. Environmental Protection Agency (U.S. EPA). To minimize the production of nitrogen dioxide and other nitrogen-based pollutants in the corona discharge device, an optimal configuration would maximize the delivery of oxygen from the pressure swing adsorption unit and minimize the delivery of ambient air that passes between the plates of the corona discharge device.

In a second embodiment of the device, an ultraviolet (UV) lamp is used to produce ozone. UV lamps produce ozone in the same manner that ozone is produced in the environment, with UV light contacting diatomic oxygen, causing the oxygen to split into two atomic oxygen atoms. These atoms react with additional diatomic oxygen molecules to form ozone. UV light is classified based on its wavelength, with ranges defined by the World Health Organization (WHO) of UV-A at 315 to 400 nm, UV-B at 280 to 315 nm, and UV-C at 100 to 280 nm. Ozone production from UV light occurs at wavelengths of around 185 nm. Typically, most commercial UV lamps consider ozone an undesirable by-product, so these lamps use a coating to block the release of wavelengths around 185 nm. In UV lamps used for ozone production, these wavelengths are maximized.

UV lamps produce light by passing electricity through a gas such as mercury. To do this, a device called a ballast converts a lower input voltage into a higher output voltage that travels across the lamp, from one electrode to another. This allows the mercury gas between the electrodes to be excited by the electricity to produce UV light. More recently, UV LEDs have also been proposed for producing UV light, although their cost has limited their use. UV lamps such as those containing mercury or argon are not selective with the type of UV light produced and must be optimized for a desired wavelength range, whereas UV LEDs can be tailored to release a very small subset of wavelengths.

Unlike corona discharge devices, UV lamps or UV LEDs produce little to no nitrogen oxides, as the wavelength of UV that splits diatomic oxygen to form ozone does not split diatomic nitrogen. This is the main benefit of producing ozone with UV lamps or UV LEDs. However, corona discharge devices are more efficient at producing ozone, capable of producing much larger quantities for a given air flow rate. Thus, careful selection of the ozone generating device is required to meet the desired application.

As an additional benefit, UV light has disinfectant properties, and is commonly used as a disinfection method. Typically, UV-C is used to kill or inactivate microorganisms by destroying nucleic acids and disrupting their DNA, leaving them unable to perform vital cellular functions. The ultraviolet light embodiment preferably utilizes a UV-C germicidal lamp that releases wavelengths of light from 150 to 280 nm, typically producing between 2.5 and 20 g/hour of ozone in a 200-cubic foot per minute (CFM) airstream. The size of the ultraviolet lamp for ozone production may be scaled accordingly to accommodate larger volumes.

Once the ozone generating device has generated the desired concentration of ozone, mixing baffles serve to thoroughly mix the airstream to increase the exposure of the pathogens to the ozonated air and to commensurately increase the potential for inactivation of the pathogens. A more complex configuration of baffles is also contemplated by this disclosure and may include additional suspended plates or rods to generate increased turbulence.

Following the mixing baffles, the disclosed apparatus utilizes a second ozone decomposition catalyst in the reactor that is used to convert ozone to oxygen. This catalyst will typically be the same as described in the alternative backflow preventer embodiment, with $MnO_2$ coated on a monolithic substrate. Table 1 below reveals the results of testing of the ozone decomposition catalyst at 30 parts per million ozone and 100 linear feet per minute (LFM) air velocity, with varying numbers of 6-inch by 6-inch by 1-inch catalyst layers.

TABLE 1

| Number of Catalyst Layers | Ozone Inlet Concentration (PPM) | Ozone Outlet Concentration (PPM) | Air Velocity (LFM) | Percentage Ozone Destruction |
|---|---|---|---|---|
| 1 | 31.23 | 7.93 | 100 | 74.61% |
| 2 | 32.45 | 0.25 | 100 | 99.23% |
| 3 | 31.18 | 0.62 | 100 | 98.01% |
| 4 | 30.51 | 0.03 | 100 | 99.90% |
| 5 | 29.38 | 0.01 | 100 | 99.97% |

Data was also gathered under the same testing criteria for higher ozone concentrations and flow rates of 60 parts per million and 90 parts per million ozone and 100 LFM and 150 LFM with the number of catalyst layers adjusted to achieve 0.02 parts per million ozone or lower on the outlet/exhaust. Table 2 provides the results of testing with additional catalyst layers.

TABLE 2

| Number of Catalyst Layers | Inlet Ozone (PPM) | Outlet Ozone (PPM) | Air Velocity (LFM) | Percentage Ozone Destruction |
|---|---|---|---|---|
| 5 | 60.87 | 0.02 | 100 | 99.97% |
| 6 | 61.80 | 0.02 | 150 | 99.97% |
| 7 | 89.35 | 0.02 | 100 | 99.98% |
| 7 | 90.34 | 0.02 | 150 | 99.98% |

Following passage through the $MnO_2$ catalyst the airstream is directed to an adsorbent for removing nitrogen oxides ($NO_x$) created by the corona discharge device. Because nitrogen oxides such as nitrogen dioxide may adversely impact individuals with compromised pulmonary systems it is critical that the concentration of nitrogen oxides be reduced as much as possible. The preferred composition of the adsorbent consists of a third monolith containing an alkaline earth metal such as barium oxide coated on a substrate; however, other catalytic compositions are also contemplated by this disclosure.

Many compounds are known for their capacity to adsorb nitrogen oxides such as NO and $NO_2$, including alkali and alkaline earth metals, activated carbons, molecular sieves, metal organic frameworks, zeolites, noble metals, soda lime (NaOH—CaO mixtures), and activated alumina. Although the preferred embodiment uses a monolithic substrate that can be coated with an $NO_x$ adsorbing compound, the adsorbent may also be used as a packed bed or in another configuration. At ozone concentrations higher than 1 part per million, nitrogen dioxide is the most common of the generated nitrogen oxides. Table 3 reveals the test results of the $NO_x$ adsorbing monolith in combination with the prior ozone decomposition catalyst, with 4 layers of the ozone decomposition catalyst coated with $MnO_2$ followed by 4 layers of coated monoliths for adsorbing nitrogen oxides. Because all the $NO_x$ compounds were oxidized to $NO_2$, the $NO_2$ concentration was recorded.

TABLE 3

NO₂ Removal Testing

| Time (Min) | Ozone Inlet Concentration (PPM) | Ozone Outlet Concentration (PPM) | NO₂ Inlet Concentration (PPM) | NO₂ Outlet Concentration (PPM) | Air Velocity (LFM) | Percentage NO₂ Removal |
|---|---|---|---|---|---|---|
| 0 | 16 | <0.005 | 1.19 | 0.01 | 85 | 99.16% |
| 60 | 16 | <0.005 | 1.14 | 0.05 | 85 | 95.61% |
| 120 | 16 | <0.005 | 1.22 | 0.10 | 85 | 91.80% |
| 180 | 16 | <0.005 | 1.23 | 0.14 | 85 | 88.62% |

In a preferred embodiment an exhaust filter may also be employed proximate the reactor's exhaust opening. This exhaust filter is employed to capture any particulates that may have eluded the pre-filter upon entry to the reactor space. Importantly, the exhaust filter is preferably not a filter with an exceedingly tight weave to avoid significantly obstructing the airflow. The filter is beneficial in capturing particulates and some de minimis percentage of still active pathogens that otherwise would have escaped into the space where the apparatus is located.

The apparatus as disclosed herein also preferably employs sensors to measure the concentrations of both ozone and nitrogen oxides. The preferred measurement locations being (i) proximate the ozone generating device, (ii) proximate the second ozone decomposition catalyst monolith utilized to convert ozone to oxygen; (iii) proximate the third adsorbent monolith for removing nitrogen oxides, and (iv) proximate the exhaust opening of the reactor. Sensors that are well known and widely available are employed to sense real-time concentrations of both ozone and $NO_x$ may also be connected to a data logger for maintenance of historical information on apparatus operation.

The apparatus as disclosed herein has undergone extensive testing to assess the efficacy of the device at removing aerosolized pathogens. In a test environment, the concentration of the viral RNA bacteriophage MS2 was measured prior to intake and upon exhaust from the apparatus to determine the percent pathogen destruction. MS2 is commonly used as a surrogate for the influenza virus and is now being considered as a possible surrogate for other RNA viruses such as SARS-CoV-2. This is due to SARS-CoV-2 being similar in size to influenza and to having an RNA genome.

A concentration of MS2 was aerosolized into a sealed environmental bioaerosol chamber containing the disclosed apparatus. An impinger instrument was used to collect samples of suspended particles in air at 0, 30, 60, 120 and 180 minutes in the chamber. All impinger samples were serially diluted, plated, and enumerated in triplicate to yield viable bioaerosol concentrations at each sampling point and time. Chamber control trial data was subtracted from the trial data to yield net LOG reduction in pathogen concentrations. The apparatus showed a consistent net LOG reduction throughout the trial with almost a full net LOG reduction at each time interval.

The average net LOG reduction went from 1.03 at the 30-minute interval to 4.12 at the 180-minute interval. A net LOG reduction over 4.00 in 180 minutes indicates the efficacy of the disclosed apparatus against the MS2 bacteriophage. See Table 4 below for a summary of the average net LOG reduction of MS2 by the device disclosed herein. The study was conducted in compliance with FDA Good Laboratory Practices which is defined at 21 CFR, Part 58.

TABLE 4

| Bioaerosol Type | Species | Surrogate | Trial ID | 30 min | 60 min | 120 min | 180 min |
|---|---|---|---|---|---|---|---|
| Virus | MS2 bacteriophage (RNA *E. coli* phage) | Influenza | 1 | −0.97 | −1.51 | −2.87 | −4.36 |
| Virus | MS2 bacteriophage (RNA *E. coli* phage) | Influenza | 2 | −0.96 | −1.50 | −2.89 | −4.08 |
| Virus | MS2 bacteriophage (RNA *E. coli* phage) | Influenza | 3 | −1.15 | −1.88 | −3.17 | −4.02 |
| Virus | MS2 bacteriophage (RNA *E. coli* phage) | Influenza | 4 | −1.04 | −1.76 | −3.05 | −4.02 |
| | | | Average | −1.03 +/− 0.08 | −1.66 +/− 0.19 | −2.99 +/− 0.14 | −4.12 +/− 0.17 |

During the trials conducted in a sealed environmental bioaerosol chamber, the room levels of ozone were also measured. See Table 5 for the Lowest, Highest, and Average output measurements of ozone across all four trials. The concentration of ozone at the exhaust opening and in the overall sealed chamber was maintained at a lower concentration than that mandated by the National Ambient Air Quality Standards (NAAQS) at 40 CFR § 50.19.

TABLE 5

| | Lowest Output (Ppm) | Highest Output (Ppm) | Average output (Ppm) |
|---|---|---|---|
| Trial 1 | 0.000 | 0.000 | 0.000 |
| Trial 2 | 0.000 | 0.000 | 0.000 |
| Trial 3 | 0.000 | 0.006 | 0.001 |
| Trial 4 | 0.000 | 0.013 | 0.000 |
| Average | 0.000 | 0.005 | 0.000 |

Additional testing conducted at MRIGlobal in February of 2021 showed that the apparatus disclosed herein had a high level of aerosol viable virus reduction of SARS-CoV-2 (the cause of COVID-19) over 99.7% for all conducted tests (maximum reduction of 99.974% for the 500 mg/m$^3$ ozone test) with a reactor flow through residence of less than 14 seconds and an ozone generation rate ranging between 250 and 1,000 mg/m$^3$ as seen in Table 6 below. The table provides that with a full turnover of air in the enclosed space, the apparatus provides an achievable net LOG reduction of active airborne pathogens within a room in the range of 4.0 to 5.0 with the net LOG reduction per pass through the device being between 2.6 to 3.4. TCID50 in the table below refers to the method used to quantify the concentration of viruses used in the test and AGI-30 refers to the type of impinger.

TABLE 6

| Ozone Generation Setting (mg/m3) | Test Number | AGI-30 Sample Location | SARS-CoV-2 TCID50/mL | Log10 TCID50/mL | Average TCID50/mL | Average Log10 TCID50/mL | Log Viral Reduction | Percent Viral Log Reduction |
|---|---|---|---|---|---|---|---|---|
| 0 | 1 | Upstream | 4.22E+03 | 3.63 | 3.34E+04 | 4.33 | 2.61 | 99.753% |
|  | 2 |  | 4.81E+04 | 4.68 |  |  |  |  |
|  | 3 |  | 4.81E+04 | 4.68 |  |  |  |  |
|  | 1 | Downstream | 6.81E+01 | 1.83 | 5.60E+01 | 1.72 |  |  |
|  | 2 |  | 3.16E+01 | 1.50 |  |  |  |  |
|  | 3 |  | 6.81E+01 | 1.83 |  |  |  |  |
| 250 | 1 | Upstream | 1.00E+04 | 4.00 | 4.01E+04 | 4.49 | 3.09 | 99.918% |
|  | 2 |  | 6.81E+04 | 4.83 |  |  |  |  |
|  | 3 |  | 4.22E+04 | 4.63 |  |  |  |  |
|  | 1 | Downstream | 3.16E+01 | 1.50 | 2.54E+01 | 1.40 |  |  |
|  | 2 |  | 2.37E+01 | 1.38 |  |  |  |  |
|  | 3 |  | 2.08E+01 | 1.32 |  |  |  |  |
| 500 | 1 | Upstream | 3.16E+04 | 4.50 | 3.71E+04 | 4.56 | 3.58 | 99.974% |
|  | 2 |  | 4.81E+04 | 4.68 |  |  |  |  |
|  | 3 |  | 3.16E+04 | 4.50 |  |  |  |  |
|  | 1 | Downstream | 3.60E+00 | 0.56 | 1.17E+01 | 0.98 |  |  |
|  | 2 |  | 1.47E+01 | 1.17 |  |  |  |  |
|  | 3 |  | 1.67E+01 | 1.22 |  |  |  |  |
| 1000 | 1 | Upstream | 3.16E+03 | 3.50 | 1.39E+04 | 4.01 | 3.44 | 99.963% |
|  | 2 |  | 1.47E+04 | 4.17 |  |  |  |  |
|  | 3 |  | 2.37E+04 | 4.38 |  |  |  |  |
|  | 1 | Downstream | 3.60E+00 | 0.56 | 3.80E+00 | 0.58 |  |  |
|  | 2 |  | 3.60E+00 | 0.56 |  |  |  |  |
|  | 3 |  | 4.20E+00 | 0.62 |  |  |  |  |

It is an object of the apparatus disclosed herein to inactivate a high percentage of airborne pathogens prior to discharging the exhausted air.

It is a further object of the apparatus as disclosed herein to economically inactivate the airborne pathogens prior to discharge from the apparatus.

It is a further object of the apparatus as disclosed herein to minimize the volume and concentration of ozone that is discharged from the apparatus to the occupied space.

It is a further object of the apparatus as disclosed herein to minimize the volume and concentration of nitrogen oxides that are discharged from the apparatus to the occupied space.

It is a further object of the apparatus as disclosed herein to scale the apparatus to inactivate pathogens in venues of any volume.

It is a further object of the apparatus as disclosed herein to inactivate airborne pathogens on a personal mobility level such that the apparatus is linked to a breathing apparatus capable of intaking ambient air and supplying it to a breathing apparatus on a personal scale.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

FIG. 16A is a perspective view of an embodiment of a monolithic substrate in a honeycomb configuration with a circular channel coated with an ozone decomposition catalyst and/or $NO_x$ adsorbing compound shown in a perspective view;

FIG. 16B is a front elevation view of an embodiment of a monolithic substrate in a honeycomb configuration with a circular channel coated with an ozone decomposition catalyst and/or $NO_x$ adsorbing compound;

FIG. 17A is a perspective view of an embodiment of a monolithic substrate in a honeycomb configuration with a corrugated channel coated with an ozone decomposition catalyst and/or $NO_x$ adsorbing compound;

FIG. 17B is an elevation view of an embodiment of a monolithic substrate in a honeycomb configuration with a corrugated channel coated with an ozone decomposition catalyst and/or $NO_x$ adsorbing compound;

FIG. 20 is a perspective view of an embodiment of the stacked assembly of four ozone decomposition catalyst layers held in place with spacers to maintain a gap between each layer;

FIG. 21 is a perspective view of an embodiment of the ozone decomposition catalyst stack showing spacing between each layer and using multiple stacks of catalysts to fill the cross-section of the apparatus;

FIG. 22 is a perspective view of an embodiment of the assembled ozone catalyst and $NO_x$ adsorbing layers held together with an outer shrink sleeve;

DETAILED DESCRIPTION

The detailed description of exemplary embodiments herein refers to the accompanying drawings, which show exemplary embodiments by way of illustration and their best mode. While these exemplary embodiments are described in sufficient detail to enable those skilled in the art to practice the inventions, it should be understood that other embodiments may be realized and that logical, chemical, and mechanical changes may be made without departing from the spirit and scope of the inventions.

The detailed description herein is presented for purposes of illustration only and not of limitation. Furthermore, any reference to singular includes plural embodiments, and any reference to more than one component or step may include a singular embodiment or step. Also, any reference to attached, fixed, connected or the like may include permanent, removable, temporary, partial, full, and/or any other possible attachment option. Additionally, any reference to without contact (or similar phrases) may also include reduced contact or minimal contact.

To inactivate pathogens, the apparatus as disclosed herein produces ozone using either a corona discharge device in conjunction with an oxygen concentrator or one or more UV-C lamps. The ozone mixes with pathogens in the airstream, causes them to be inactivated. Once the pathogens are inactivated, ozone and any other by-products such as nitrogen oxides are removed. The apparatus has undergone extensive testing to ensure uniform ozone production, high pathogen inactivation, and removal of both ozone and nitrogen oxides.

Figure 1:
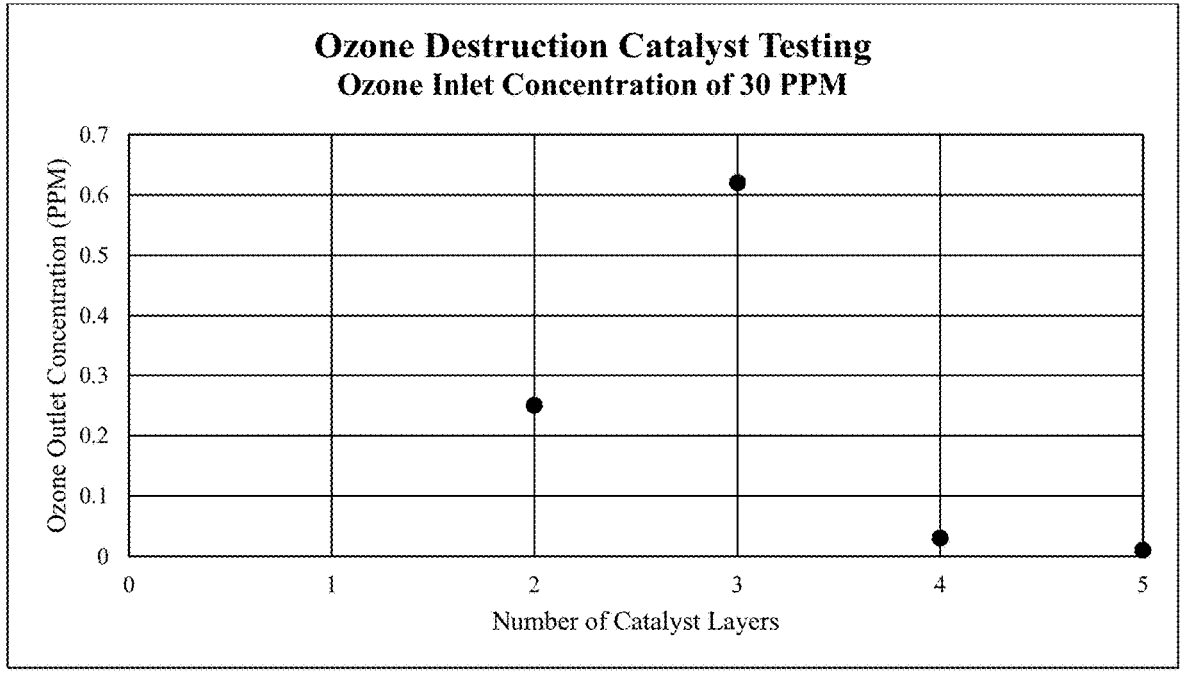
FIG. 1 is a graph of experimental data illustrating the concentration of ozone at the outlet of the apparatus relative to the number of catalyst layers.
Figure 2:
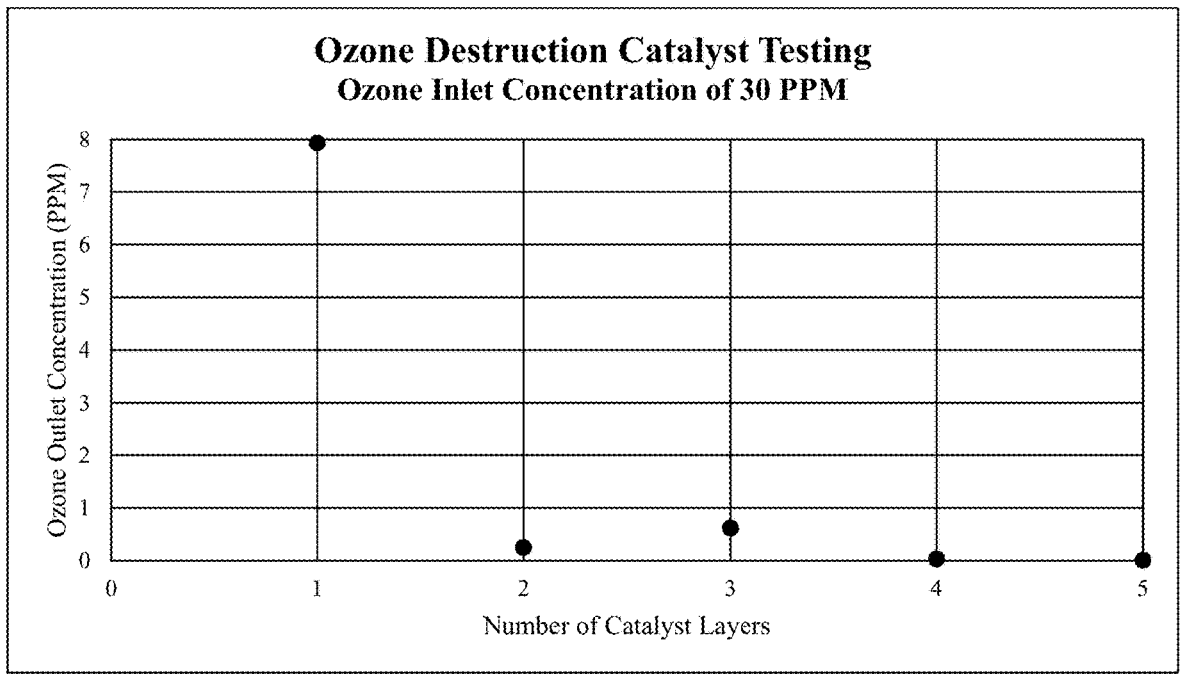
FIG. 2 is a graph of experimental data illustrating the concentration of the ozone at the outlet of the apparatus relative to the number of catalyst layers.

FIG. 1 shows the performance of the ozone decomposition catalyst in removing 30 parts per million ozone from an airstream at 100 linear feet per minute (LFM) air velocity. The number of catalyst layers, and thus the total volume of catalyst, are varied to illustrate increased ozone removal per layer. Each catalyst layer is 6 inch by 6 inch by 1 inch in size. At 5 catalyst layers, up to 99.9% of the ozone is removed from the airstream. FIG. 2 illustrates the same data as described in FIG. 1 but is expanded to show the performance of a single layer of catalyst in removing ozone from the airstream.

Figure 3:
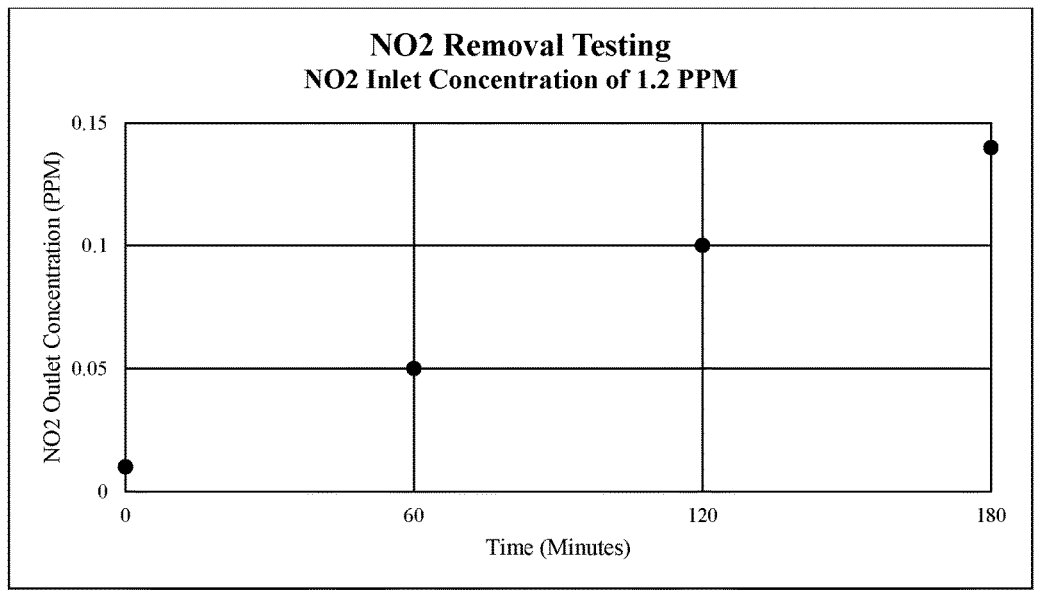
FIG. 3 is a graph of experimental data illustrating the concentration of nitrogen dioxides relative to the amount of reaction time.

FIG. 3 illustrates the performance of the NOx adsorbent in removing any nitrogen oxides, in this case nitrogen dioxide, which are produced along with ozone in the apparatus. An airstream containing 1.2 parts per million nitrogen dioxide was passed through the NOx adsorbent at 85 LFM for 180 minutes. The concentration of nitrogen dioxide was monitored at the outlet of the NOx adsorbent and shown to be at 0.05 parts per million for the entire test, well below the one-hour maximum concentration of 100 parts per billion (PPB) set by the U.S. EPA.

Figure 4:
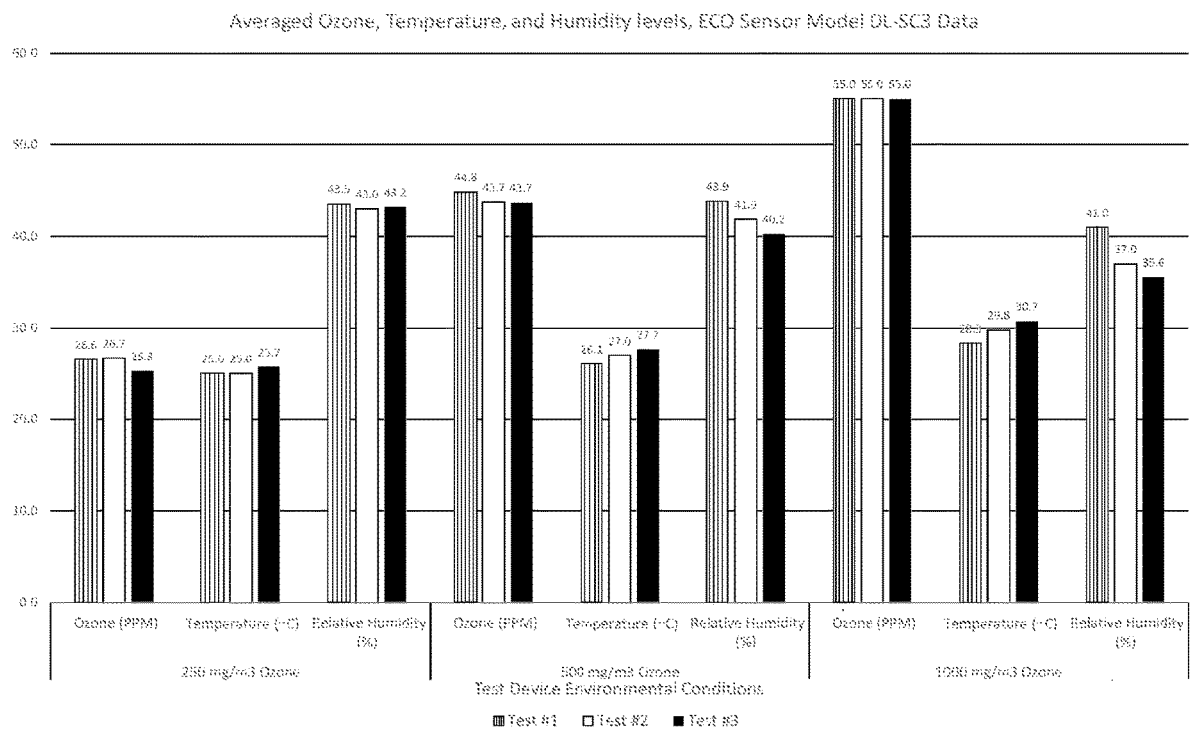
FIG. 4 is a bar graph illustrating test results for a Model DI-SC3 ECO ozone sensor to include ozone concentration (PPM), temperature (° C.), and relative humidity (%)
Figure 5:
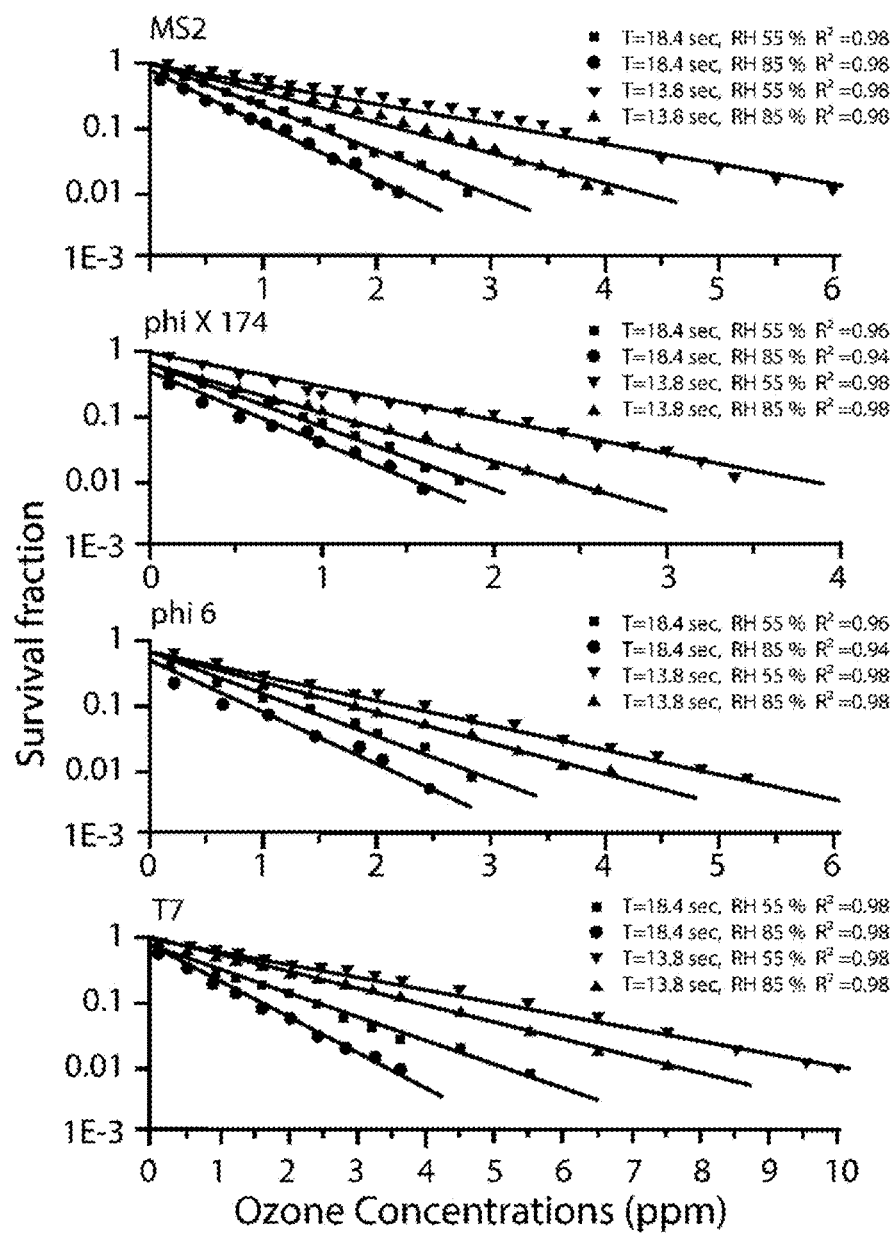
FIG. 5 is a series of graphs illustrating the survival fraction of pathogens relative to ozone concentration.
Figure 6:
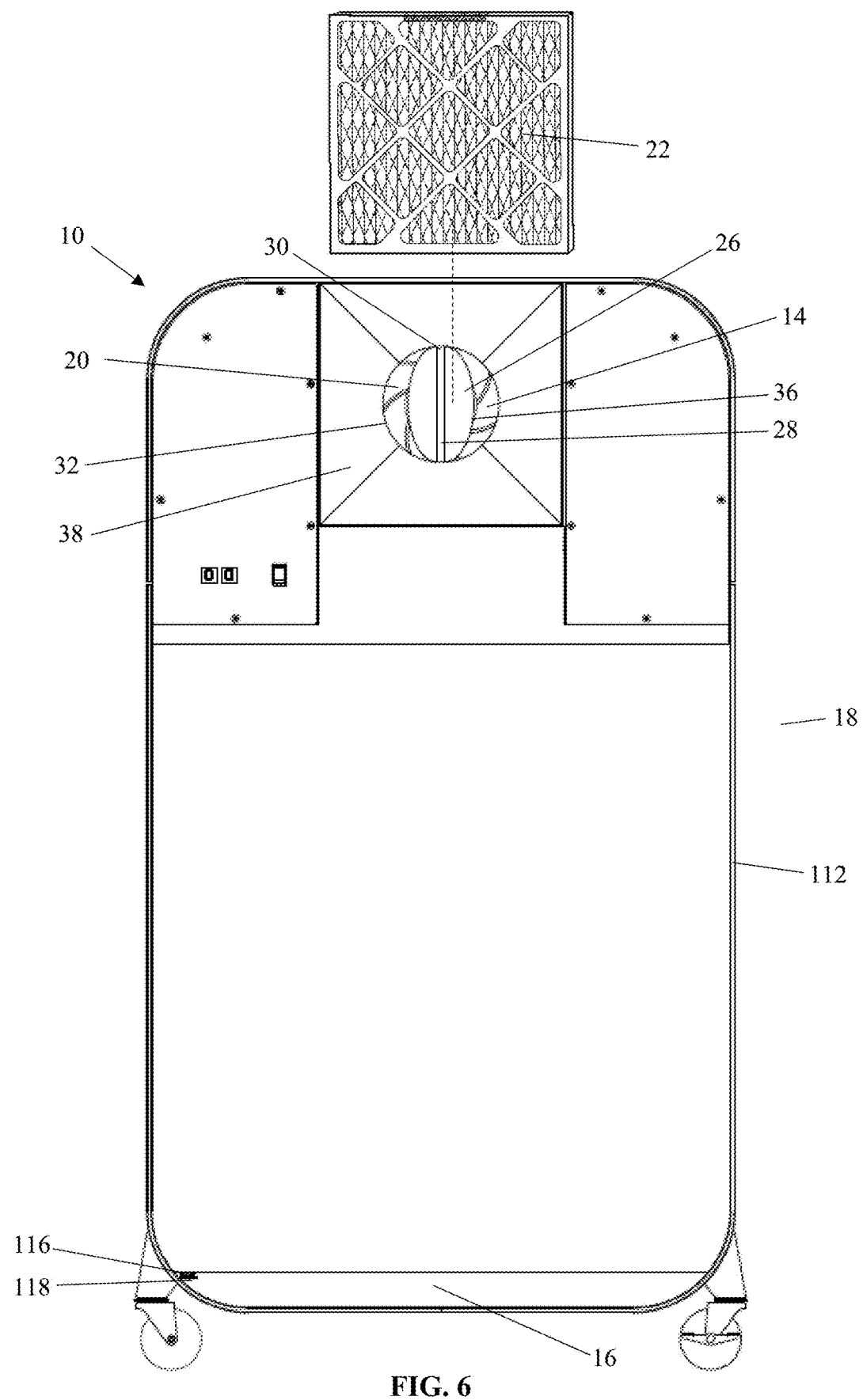
FIG. 6 is a front elevation view of an embodiment of the pathogen inactivation apparatus with the front panel and pre-filter removed to show the backflow preventer and inlet fan.
Figure 7:
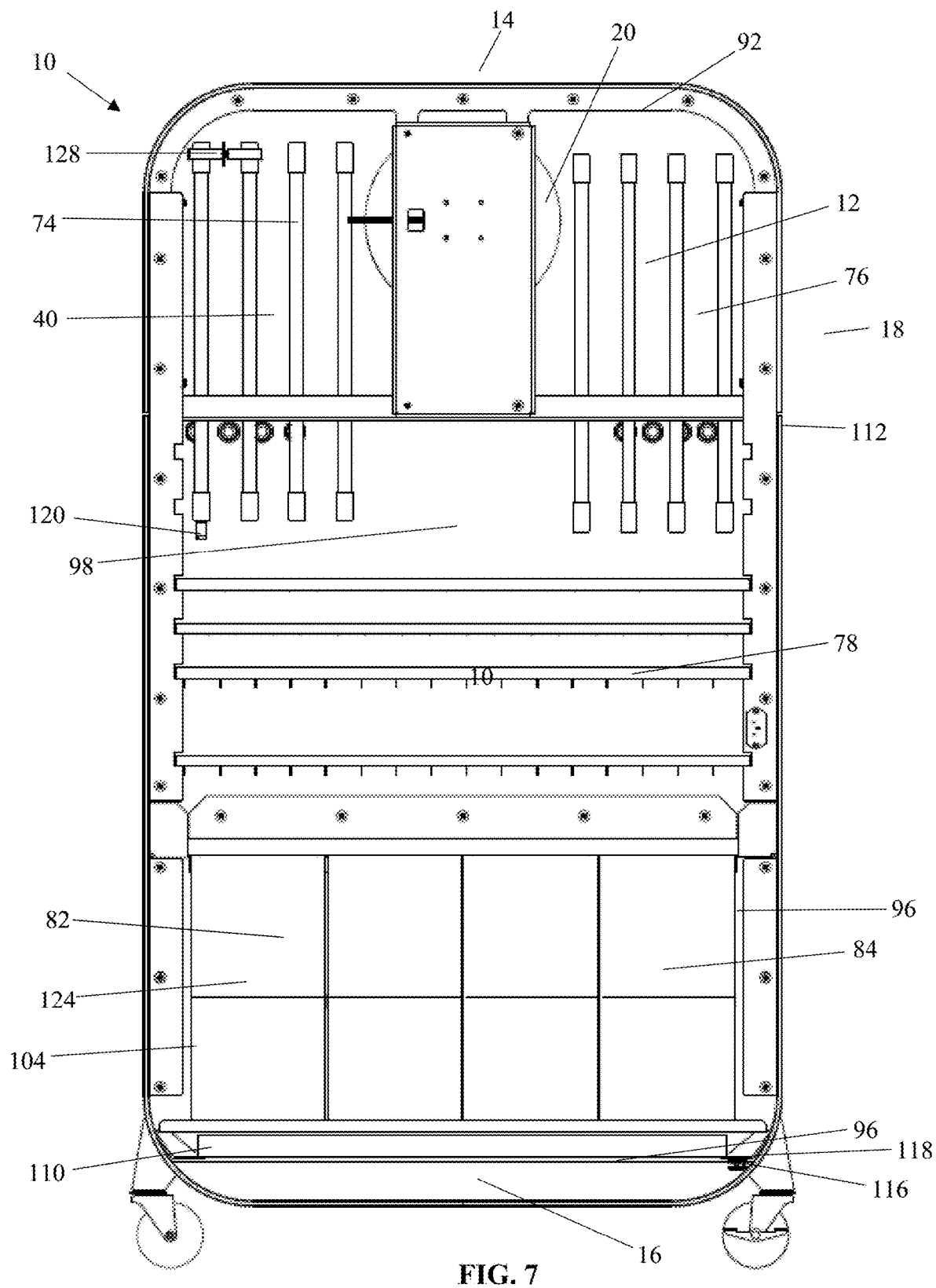
FIG. 7 is a rear elevation view of an embodiment of the pathogen inactivation apparatus illustrating functional components.

The $mg/m^3$ ratings for ozone generators are measured when they are used with a concentrated oxygen supply of 90% to 99%. Since ambient air contains only around 21% oxygen, ozone generators often produce far less ozone than the rating supplied by their manufacturer. To account for this and other environmental conditions, sensors for Temperature (° C.), Relative Humidity (%), and Ozone (PPM) were built into the Test Device. As seen in FIG. 4, the ozone sensor (ECO Sensor Model DL-SC3) measured a range of 25 to 55 parts per million across the tests.

Concentrations of ozone below 25 parts per million have likewise been shown in published academic studies to inactivate over 99% of airborne pathogens. One study in particular—Chun-Chieh Tseng & Chih-Shan Li (2006) *Ozone for Inactivation of Aerosolized Bacteriophages, Aerosol Science and Technology,* 40:9, 683-689, published by the American Association for Aerosol Research, disclosed that for 99% virus inactivation of phi 6, phi X174, MS2, and T7 required ozone doses of 2.50 parts per million, 3.84 parts per million, 6.63 parts per million, and 10.33 parts per million, respectively with a contact time of 13.8 seconds. FIG. 5 depicts the survival fraction of airborne MS2, phi X174, phi 6, and T7 exposed to different ozone concentrations at relative humidities of 55% and 85%.

The apparatus 10 as illustrated in FIG. 6, may be located anywhere a continuous stream of air requires the inactivation of airborne pathogens. Such locations may include residential, commercial, and industrial settings. This apparatus may also be employed in mobile settings such as on planes and trains that experience a substantial turnover of passengers frequently, some of whom may be carriers of contagious pathogens.

The apparatus 10, as further illustrated in FIG. 7, includes a reactor 12 that forms an enclosed chamber in which the pathogen inactivation and catalytic conversion/adsorption functions to be described below occur. The reactor may be of many different cross sections such as round, square, or rectangular. The exterior of the reactor is preferably fabricated from sheet metal; however, other materials such as plastic or composites are contemplated by this disclosure. The interior of the reactor 12 and resident components must be composed of materials that are compatible with ozone, as ozone is capable of oxidizing many materials, leading to their degradation.

The reactor 12 has an intake opening 14 and an exhaust opening 16. Ambient air 18 is drawn into the reactor 12 through the intake opening 14 and after passing through the various zones of the reactor 12 passes out through the exhaust opening 16 with a high percentage of the airborne pathogens inactivated and therefore substantially reducing the potential for infecting those in the surrounding spaces.

As shown in FIG. 8, ambient air 18 is drawn into the reactor 12 by an internally mounted fan 20. The fan 20, as disclosed herein, preferably covers the cross-sectional opening of the interior of the reactor 12; however, alternative configurations are also contemplated by this disclosure. The fan 20 is preferably mounted inside of the reactor 12 opening to allow installation of a removable pre-filter 22 in front of the fan 20. However, some embodiments may use a fan 20 mounted outside of the reactor 12, such as those that integrate within existing HVAC systems. The pre-filter 22 may be readily removed and replaced and is not of such a tight weave to adversely impact the ability of the fan 20 to draw ambient air past the pre-filter 22.

As illustrated in FIGS. 9A and 9B the apparatus 10 also employs a backflow preventer 26 that restricts the ability of air that has entered the reactor 12 from escaping back out through the intake opening 14. The backflow preventer 26 may be as simple as a flapper valve 28 configuration that can flex inwardly on three sides with the top edge 30 secured to the reactor interior space 32. Should there be a reversal of airflow, for whatever reason, the outer edges 36 of the flapper valve 28 will seal against a flange 38 on the three sides that are unconnected to the reactor interior space 32 thereby preventing outward airflow. The objective of installing a backflow preventer 26 is to prevent the release of highly ozonated air, or air containing high levels of nitrogen oxides, from entering the room or space that is undergoing pathogen inactivation with the disclosed apparatus 10. A separate backflow preventer 26 embodiment is also contemplated below for removing ozone from air without limiting airflow through the intake.

Ozone generation occurs in area 40 interior to the reactor 12 away from the intake opening 14 and beyond the backflow preventer 26. In this area 40, as illustrated at FIG. 7 there are multiple embodiments of ozone generating equipment that are contemplated. A first embodiment, as illustrated in FIG. 10, utilizes a corona discharge device 42. A corona discharge device operates by applying a voltage between two electrodes, causing air between the electrodes to be ionized. This ionization splits diatomic oxygen, producing an oxygen molecule that reacts to form ozone.

In operation, the fan 20 moves the airstream 98 into the space gap 44 between the corona discharge plates 50 where the high voltage, high frequency and alternating current results in the generation of ozone molecules 76. It is ozone that serves to inactivate the airborne pathogens within the reactor 12. In an alternative embodiment, as further illustrated in FIG. 11, a heat sink 48 is optionally secured to the corona discharge device 42. The heat sink 48 serves to cool the plates 50 of the corona discharge device by radiating heat through fins 52 of the heat sink 48 resulting in the production of a higher concentration of ozone and thereby increased inactivation of the airborne pathogens.

Alternative cooling of the heat sink such as with a supplemental fan or water-cooling device yields even higher ozone concentrations and therefore increased inactivation of airborne pathogens. The methodologies described above for cooling the corona discharge device 42 are all contemplated by this disclosure.

An alternative embodiment of the apparatus 10 employs a corona discharge device 42 in combination with an oxygen concentrator 54 utilizing "pressure swing adsorption." An exemplary oxygen concentrator configuration is shown in FIGS. 12A and 12B. An oxygen concentrator 54 is disposed proximate to the corona discharge device 42 to facilitate the introduction of highly concentrated oxygen between the plates 50 of the discharge device 42. As is discussed in greater detail below, a significant percentage of the nitrogen is removed from the oxygen airstream exiting an oxygen concentrator.

With a substantially reduced percentage of nitrogen passing between the plates 50 of the corona discharge device 42 there is a greatly reduced potential for nitrogen oxides to be produced from the corona discharge device 42. Since nitrogen oxides are considered air pollutants and are regulated by the U.S. Environmental Protection Agency at 40 CFR § 50.11, there is a human health based reason, specifically a pulmonary concern, to increased exposure to high concentrations of nitrogen oxides. The 8-hour standard for the National Primary ambient air quality standard for nitrogen oxides codified at 40 CFR § 50.11 provides that the concentration of nitrogen oxides in the ambient air shall not exceed 53 parts per billion and the one-hour standard provides that the concentration of nitrogen oxides shall not exceed 100 parts per billion. The airstream 98 exiting the apparatus 10 as disclosed herein ejects the airstream to the ambient air 18 with a concentration of nitrogen oxides less than 100 parts per billion.

Figure 13A:
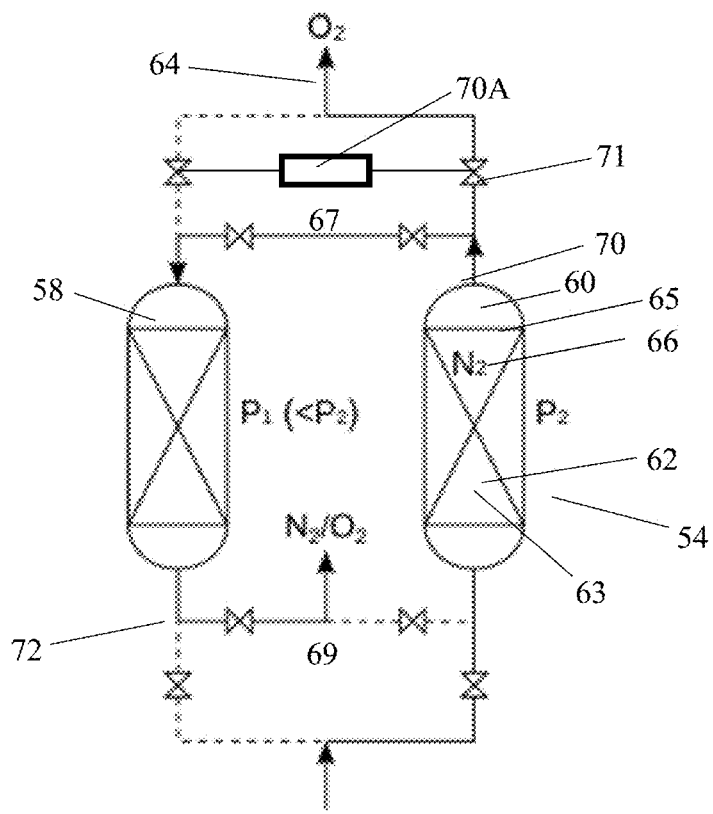
FIG. 13A illustrates a schematic the operation of an embodiment of a pressure swing adsorption apparatus with the left side being regenerated while the right side adsorbs nitrogen and releases concentrated oxygen out the top.
Figure 13B:
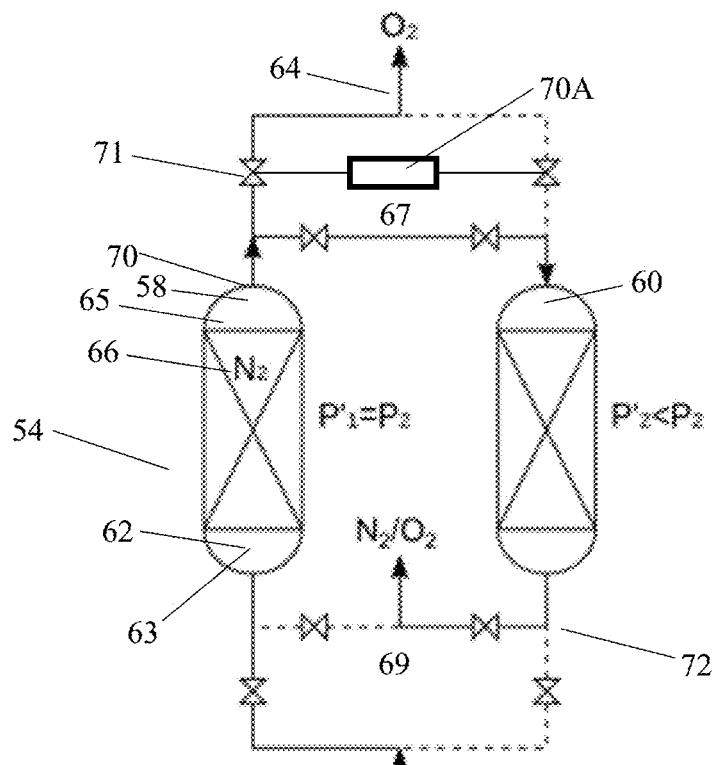
FIG. 13B is a schematic of the operation of an embodiment of a pressure swing adsorption apparatus with the right side being regenerated while the left side adsorbs nitrogen and releases concentrated oxygen out the top.

As illustrated in FIGS. 13A and 13B, the oxygen concentrator 54 relies upon at least two vessels 58, 60 that alternate being under pressure usually from 50 to 150 psi and the second being at or near atmospheric pressure. While the first vessel is being pressurized the second vessel is depressurized, hence the reason for the use of the term "swing" in the name of the identified technology. Zeolite 62 is a mineral consisting of aluminum and silicon compounds that contain micropores that absorb nitrogen from the air. The zeolite serves to separate the nitrogen from the oxygen at a molecular level.

FIG. 13A illustrates the initial adsorption step of the right vessel 60. In the right vessel, the unwanted nitrogen is adsorbed by the zeolite 62 which is positioned in the form of a bed 63 at the base of each vessel 58, 60. What remains in the vessel space 65 above the zeolite bed 63 is primarily oxygen 64. This oxygen 64 can then be routed out of the top 70 of the pressurized vessel 60 and into the corona discharge device without concern for the formation of significant concentrations of nitrogen oxides, i.e., $NO_2$, NO, $N_2O_5$, etc. The oxygen from the pressurized vessel enters the corona discharge device 42 at a flow rate that optimizes the production of ozone and minimizes the production of nitrogen oxides. The nitrogen 66 adsorbed in the zeolite bed 63 can also be routed for discharge, for example, into the building space without threat of harm to human health as the nitrogen 66 entering into the room atmosphere does not present a pulmonary risk as do nitrogen oxides.

Once zeolite 62 has adsorbed a maximum concentration of nitrogen 66, the left vessel 58 is pressurized and the process is repeated within the left vessel 58. As shown in FIG. 13B, the zeolite 62 absorbs nitrogen 66 from the pressurized air and the concentrated oxygen 64 is evacuated near the top 70 of the vessel for routing to the corona discharge device 42. During this time, the pressure is released within the right vessel 60, allowing adsorbed nitrogen to desorb from the surface of the zeolite 62 and into the atmosphere. Nitrogen 66 is evacuated at the bottom 72 of both vessels 58, 60 through an exhaust port 69 that leads to the environment. The exhausting of nitrogen 66 to the ambient air does not contribute to pulmonary distress because the atmosphere already contains roughly 78% nitrogen.

It is contemplated by this disclosure that, in at least one embodiment, a portion of the overall airstream passing through the corona discharge device 42 is the oxygen continuously routed from the vessels of the oxygen concentrator 54. With highly purified oxygen entering the corona discharge device 42 from the oxygen concentrator 54 the corona discharge device 42 is capable of producing ozone at concentrations ranging from 1,000 to 60,000 parts per million. This highly concentrated ozone is commingled with the airstream 98 passing through the reactor 12 thereby reducing the overall concentration of ozone for inactivating the pathogens. To minimize the production of nitrogen dioxide and other nitrogen oxides in the corona discharge device 42 an optimal configuration directs the delivery of oxygen 64 from the oxygen concentrator 54 and minimizes the delivery of ambient air that passes through the plates 50 of the corona discharge device 42. The rationale for this being that ambient air contains roughly 78% nitrogen while the gas supplied by the oxygen concentrator 54 contains a very high percentage of oxygen 64 with little nitrogen 66 available for conversion to nitrogen oxides in the corona discharge unit.

In another embodiment, the oxygen concentrator 54 utilizes a continuously variable control valve, also known as a proportional isolation valve 71, is illustrated at FIGS. 13A and 13B. The valve 71 is operable to meter the volume of oxygen per unit of time delivered from the oxygen concentrator 54 to the corona discharge device 42. This type of valve 71 is well known in the industry. An exemplary valve is the Eclipse proportional isolation valve model EIVU-M-V sold by Clippard.

This embodiment may also employ a microcomputer, a microcontroller, or a programmable logic controller 70A that is in communication with the valve 71 to control the volumetric flow of oxygen 64 through the valve 71 to the corona discharge device 42. Implementation of such controllers is well known in the industry and need not be detailed herein. Fine variable control of the valve 71 facilitates control of the production of ozone by the corona discharge device 42 as well as limiting the production of nitrogen oxides. An exemplary programmable logic controller 70A for use in this application is sold by Clippard such as the SCPVD-1 Stepper-Controller Proportional Valve Driver.

This fine level of control is accomplished by utilizing the valve 71 to balance the displacement of ambient air with oxygen 64 from the oxygen concentrator 54. Signals from the ozone and nitrogen oxides sensors (discussed in greater detail below) mounted within the reactor 12 will provide input to the programmable logic controller, microcomputer, or microcontroller to optimize operational inflow of oxygen 64 to the corona discharge device 42.

Figure 14:
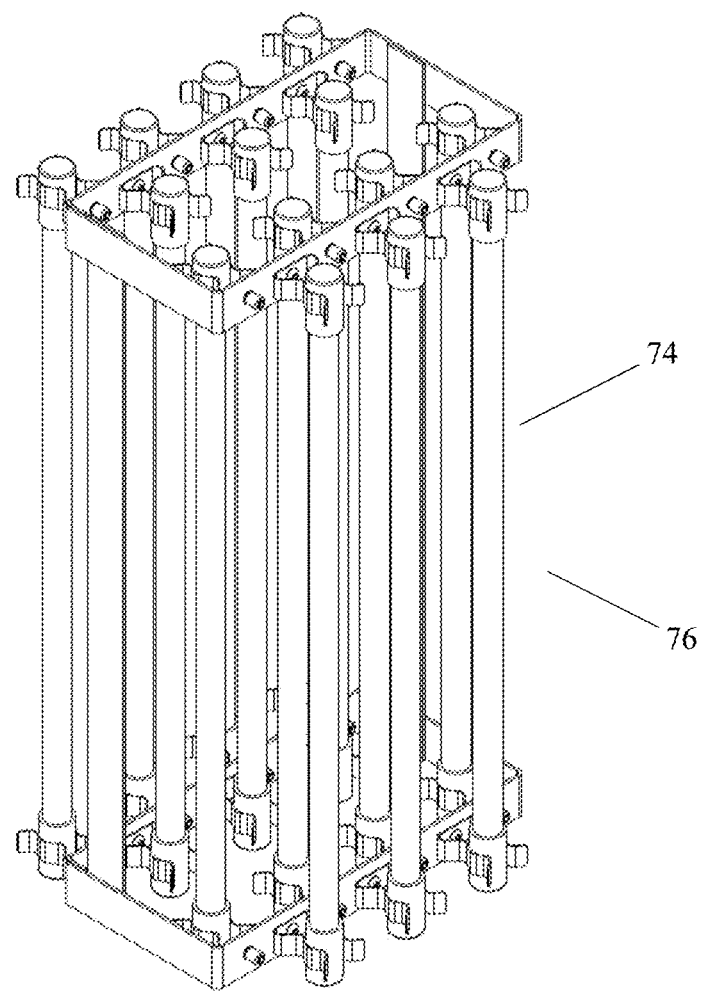
FIG. 14 is an embodiment of a bank of UV-C ozone generators.
Figure 15:
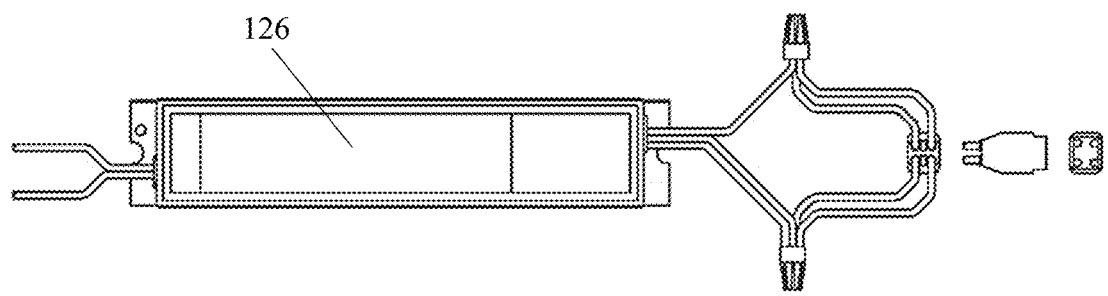
FIG. 15 is a schematic of a ballast and wiring to provide high voltage to the UV-C ozone generators.
Figure 18:
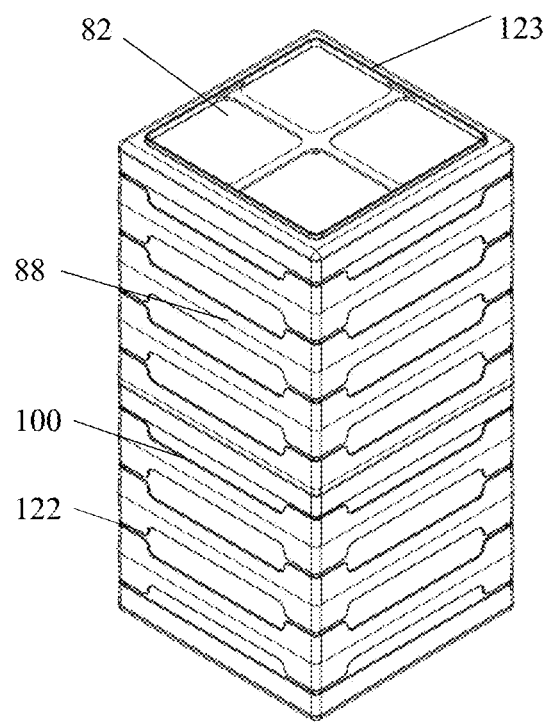
FIG. 18 is a perspective view of an embodiment of the assembly of a plurality of ozone catalyst layers and NOx adsorbing layers held in position with spacers.
Figure 19:
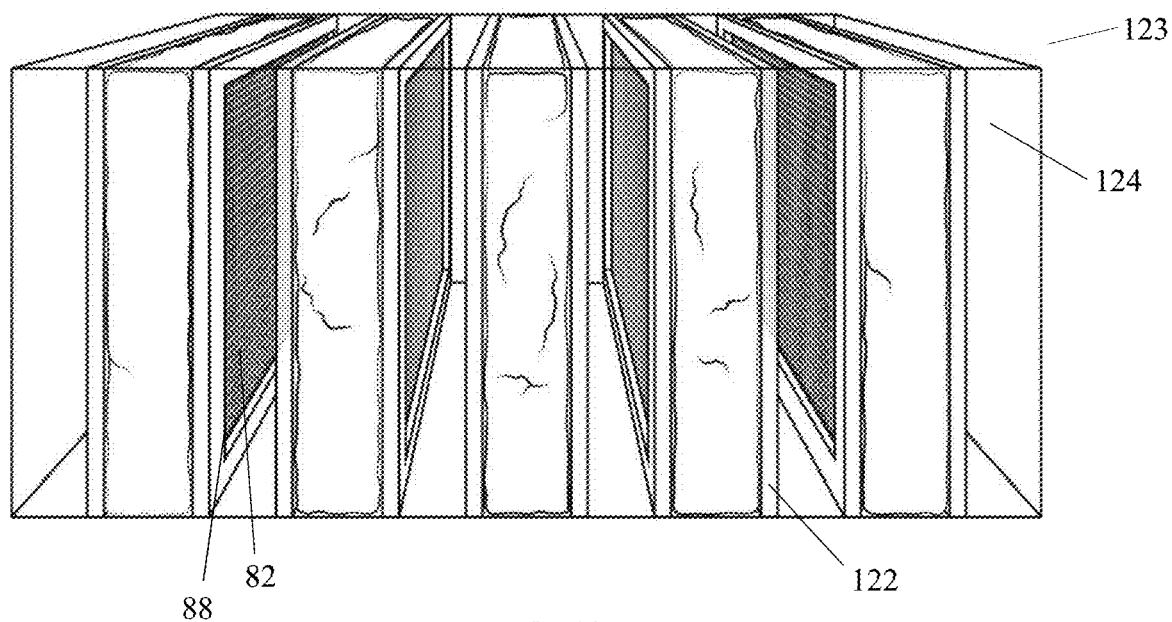
FIG. 19 is a side perspective view of an embodiment of the ozone decomposition catalyst stack showing spacing between the substrate layers.

Another embodiment contemplated by the disclosure for ozone generation within the reactor 12 is by using ultraviolet light. Lamps that produce ozone from ultraviolet light maximize the production of wavelengths around 185 nm. These lamps also produce many other wavelengths of light in the UV-C spectrum. In contrast to ozone generators using corona discharge, UV-C lamps produce little to no nitrogen oxides, although they are less efficient, producing smaller concentrations of ozone for a given airstream. The ultraviolet light embodiment preferably utilizes UV-C germicidal lamps that produce, for example, between 2.5 to 20 g/hour of ozone and with an airflow rate of about 200 CFM for a 500 to 1,500 $ft^3$ space in a residence, office, or industrial setting. FIG. 14 shows an example of an array of UV-C lamps 74 comprising the ozone generator within the apparatus 10. The array of UV-C lamps is powered using devices called ballasts, which increase the lower input voltage to a higher output voltage to ensure the mercury gas is excited to release UV light. An exemplary ballast 126 is shown in FIG. 15.

Figure 8:
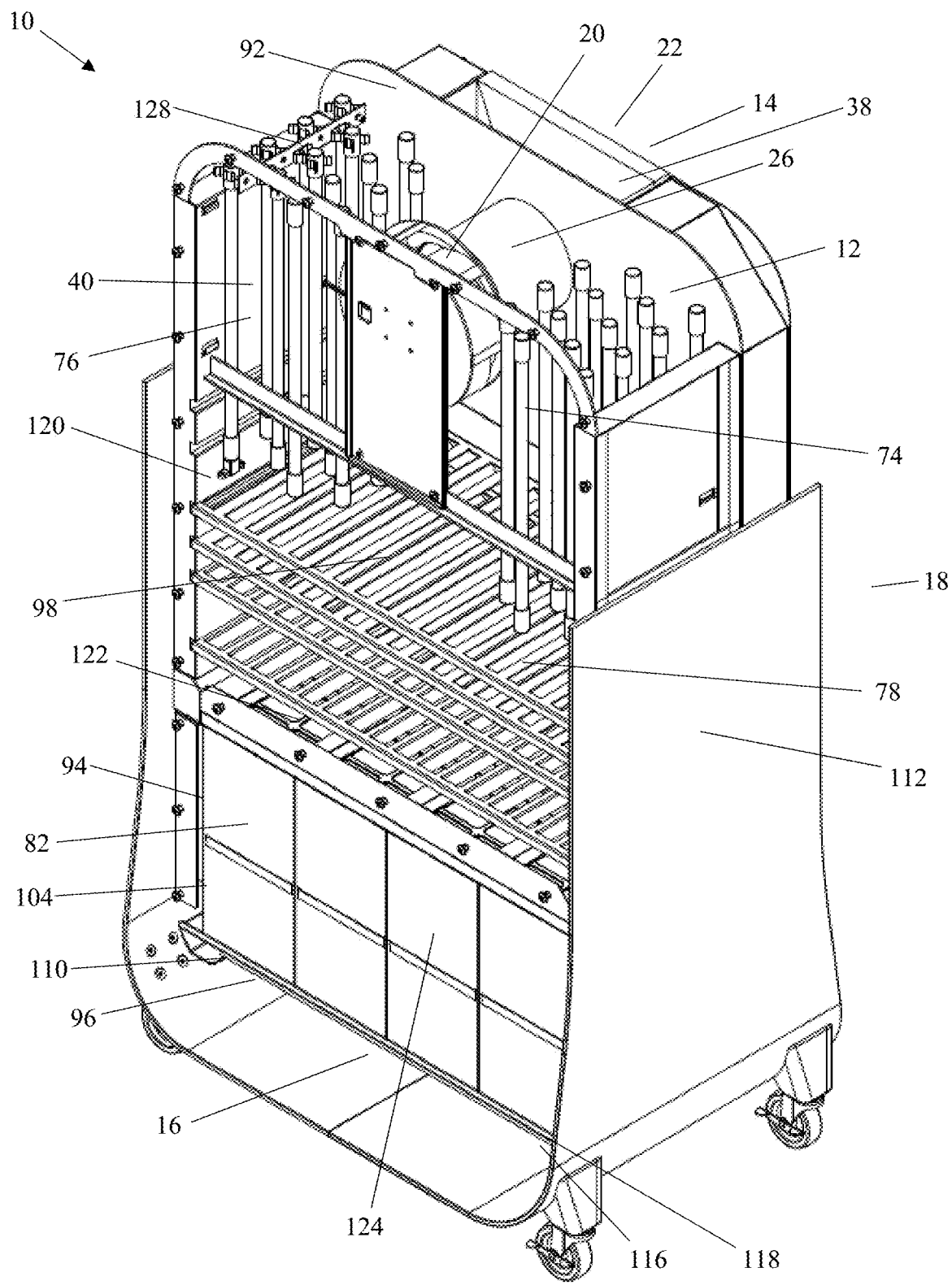
FIG. 8 is a top cutaway perspective view of an embodiment of the pathogen inactivation apparatus illustrating functional components.
Figure 9A:
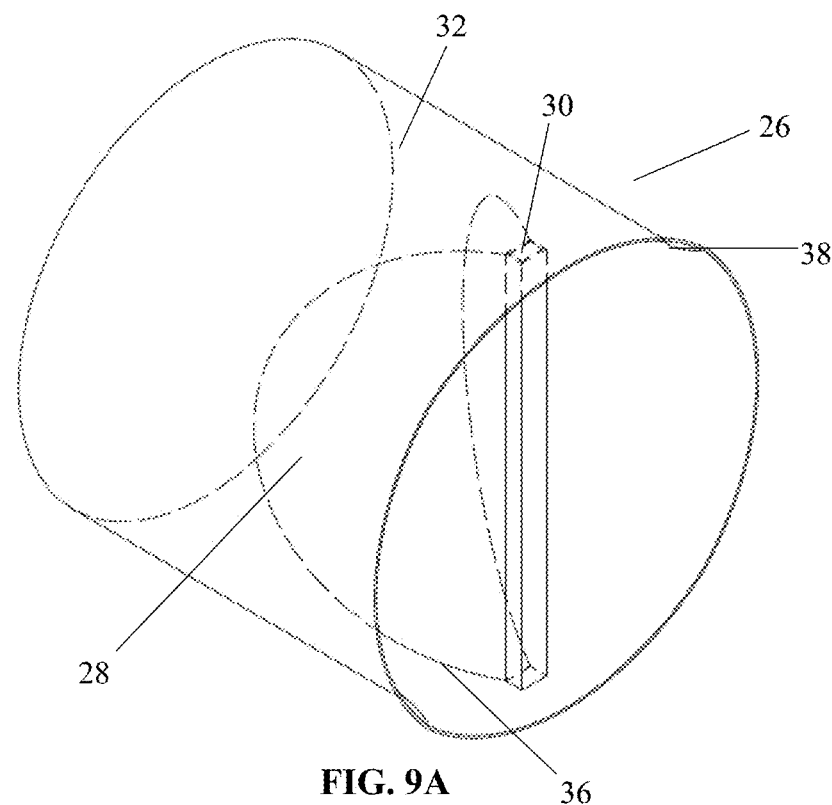
FIG. 9A is a perspective view of an embodiment of a backflow preventer with the flapper valve in the open position.
Figure 9B:
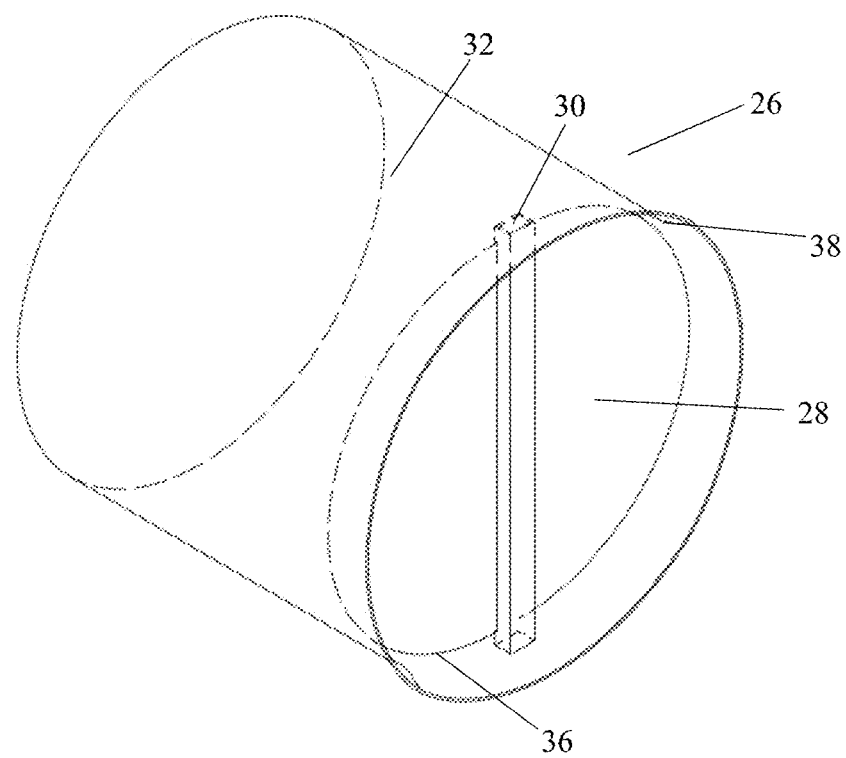
FIG. 9B is a perspective view of an embodiment of a backflow preventer with the flapper valve in the closed position.
Figure 10:
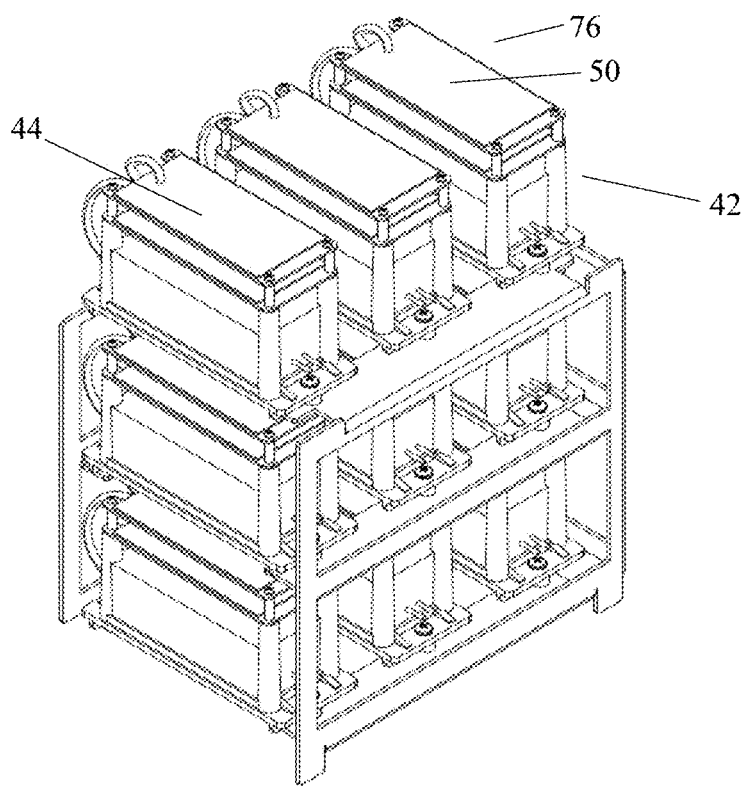
FIG. 10 is a perspective view of an embodiment of a corona discharge device.
Figure 11:
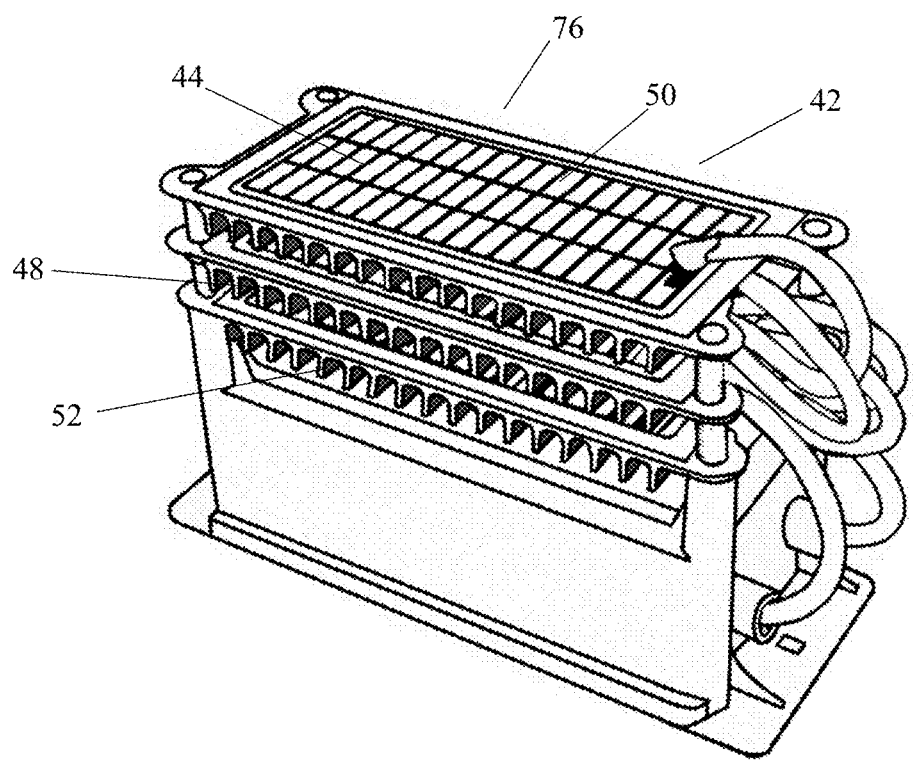
FIG. 11 is a perspective view of an embodiment of a corona discharge device with an associated heat sink secured thereto.
Figure 12A:
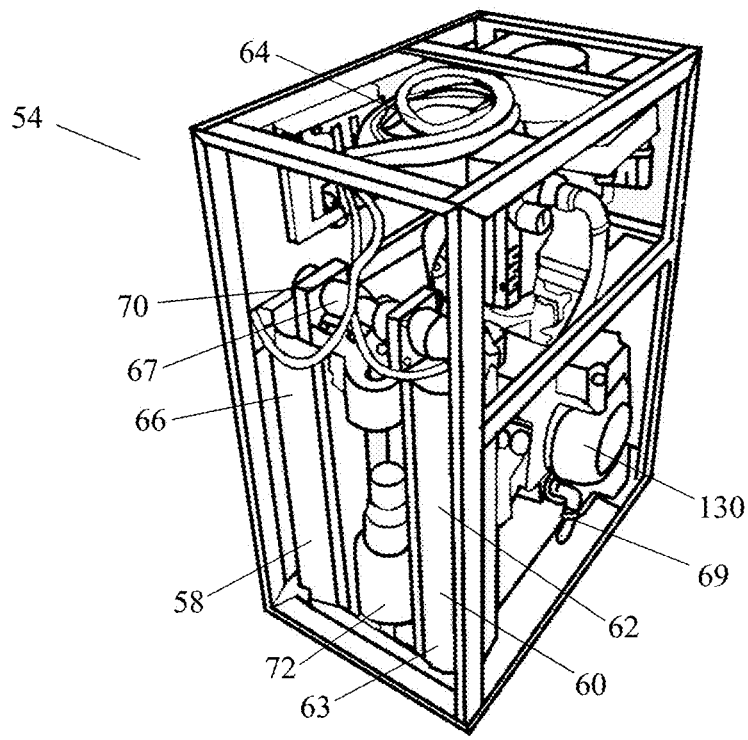
FIG. 12A is a perspective view of an embodiment of an oxygen concentrator.
Figure 12B:
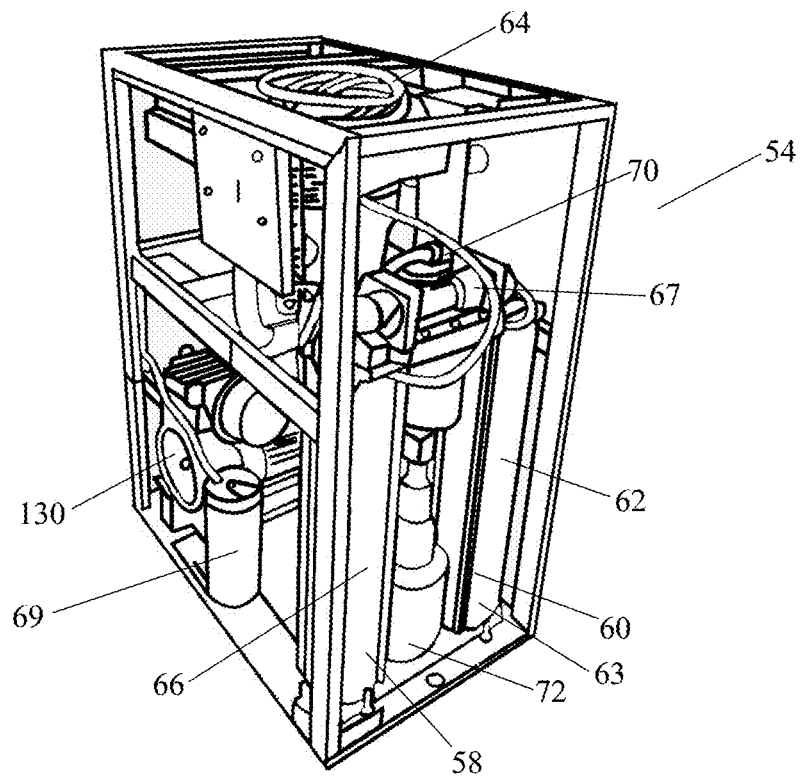
FIG. 12B is a further perspective view of an embodiment of an oxygen concentrator.

The size of the UV-C device may be scaled accordingly to accommodate larger volumes. Multiple vendors produce UV-C lamps that can produce up to 3 g/hour of ozone. As illustrated in FIG. 8, the UV-C ozone generator lamps 74 are positioned within the reactor 12 and intake air 18 is passed around the plurality of ozone generator lamps 74 thereby creating ozone 76 for use in inactivation of airborne pathogens.

Following generation of the ozone 76, the ozonated and the pathogen laden air is moved over and around at least one baffle 78 within the reactor 12 to provide for thorough mixing and contact of the pathogens with ozone. The concentration of ozone 76 within the reactor 12, proximate the ozone generator, is in the range of 1 to 55 parts per million, a concentration that is sufficient to inactive a very high percentage of the airborne pathogens transiting through the reactor 12. A single plate baffle 78 with multiple channels or a plurality of long cutouts may suffice to create the desired mixing. Multiple baffles in series are also contemplated to achieve thorough mixing; however, with increasing baffle placement comes the need for increased fan output to drive the airflow through the reactor. Additional baffle configurations are contemplated by this disclosure and multiple configurations may be employed to increase the exposure of the pathogens to ozonated air. As indicated above, when the airborne pathogens are exposed to an ozone concentration of between 1 and 55 parts per million, they are rapidly inactivated by such exposure.

Once thorough mixing has been completed and sufficient residence time has passed for the ozone to inactivate the pathogens in the airstream, the airstream containing the inactivated pathogens and their components and any excess ozone 76 is exposed to an ozone conversion decomposition catalyst 82 for converting the ozone 76 to oxygen. It is critical to remove as much ozone as possible from the airstream because ozone is considered an air pollutant according to federal regulation at 40 CFR § 50.19 and exposure of 1 hour is limited to a concentration no greater than 70 parts per billion.

As illustrated in FIGS. 16A and 16B, an ozone decomposition catalyst 82 such as manganese dioxide ($MnO_2$) is coated on a honeycomb monolithic substrate 88 for converting ozone to oxygen. The ozone decomposition catalyst monolith 88 is made of a ceramic such as cordierite containing honeycomb shaped channels 90 allowing for maximum contact between the catalyst and the advancing airstream 98, optimizing ozone conversion. FIGS. 17A and 17B show an alternative monolithic substrate made of metal in a configuration with corrugated channels 90A. As illustrated in FIGS. 7 and 8, the ozone decomposition catalyst 82 is preferably disposed within the reactor 12 in such a manner that it can be easily withdrawn and replaced such as through a slot 92 in the top or side 94, 96 of the reactor 12. Catalysts other than $MnO_2$ and configurations other than a monolithic substrate 88 with channels 90, 90A are also contemplated by this disclosure.

Once the airstream 98 advances beyond the ozone decomposition catalyst 82 it may still be laden with nitrogen dioxide and other associated nitrogen oxides, i.e., NO, $N_2O_5$, etc., that are harmful to human pulmonary function. Both the ceramic and metallic monolithic substrates 88 as shown in FIGS. 16A, 16B, 17A and 17B can support a coating with an $NO_x$ adsorbent compound 102 such as barium oxide or potassium oxide or combinations of the two compounds, as well as the previously described ozone decomposition catalyst 82. In this way, the uniform nature of the ozone decomposition catalyst 82 and the $NO_x$ adsorbent 102 allows for easier maintenance and replacement. Other catalysts for adsorption of the nitrogen dioxide, and associated nitrogen compounds, are also contemplated by this disclosure, such as various alkali and alkaline earth metals, activated carbons, molecular sieves, metal-organic frameworks, zeolites, noble metals, soda-lime (NaOH—CaO mixtures), and activated alumina. FIG. 18 shows a module 123 containing various layers of ozone decomposition catalyst monoliths 88 and NOx adsorbing monoliths 100. Each layer contains a monolithic substrate as shown in FIG. 16A, 16B, 17A, or 17B coated with one ozone decomposition catalyst 82 or NOx adsorbent compound 102. In this way, the number of ozone decomposition catalyst monoliths 88 and NOx adsorbing monoliths 100 may be varied depending on the requirements of the application.

FIG. 19 illustrates monolithic layers containing several ozone decomposition catalyst-coated 82 monolithic substrates 88 separated by spacers 122 within the same module stack 123. FIG. 20 illustrates how a module 123 may be fabricated to scale for increases in air flow rate as well as ozone concentrations. FIG. 21 illustrates a module 123 with nominally and preferably half-inch spacers 122 between each monolith containing both ozone decomposition catalyst monoliths 88 and $NO_x$ adsorbing monoliths 100.

In a preferred embodiment, several ozone decomposition catalyst monoliths 88 are placed before the nitrogen oxides adsorbing monoliths 100 to ensure that ozone does not compete with nitrogen oxides for adsorption sites. FIG. 22 illustrates the combined module 123 of FIG. 18 wrapped within a shrink sleeve 124 to ensure stability and maintain performance. The shrink sleeve 124 prevents exfiltration of the airstream 98 out and around the catalytic and adsorption processes thereby improving the overall performance of the apparatus 10.

With the combined monoliths 88, 102 within a module 123 and the stacking of such modules, both the ozone decomposition catalyst monoliths 88 and the $NO_x$ adsorption monoliths 100 are preferably positioned within the reactor 12 in such a manner that they can be extracted from the reactor 12 through a slot 104, as illustrated at FIGS. 7 and 8, for replacement or refurbishment, should such maintenance be required.

Once the adsorption of the nitrogen oxides has been accomplished the airstream 98 optionally advances to an exhaust filter 110, such as illustrated at FIG. 24. As illustrated at FIGS. 7 and 8, the exhaust filter 110 is incorporated into the design to capture any entrained particulates that may have passed through the pre-filter or become entrained in the airstream 98 through tiny gaps or openings in the walls 112 of the reactor 12. The exhaust filter 110 may also include a coating such as activated carbon to remove any odor producing compounds that are present within the airstream 98.

The exhaust filter 110 is preferably in the range of a minimum efficiency reporting value (MERV) of 7-16 and is capable of trapping air particles in the 0.3 to 1.0-micron size range but of not such a high MERV rating that it is difficult for the apparatus 10 to exhaust the airstream 98 out of the reactor 12. The exhaust filter 110 is preferably disposed within the reactor 12 in such a manner as with the ozone decomposition catalyst monolith 82 and $NO_x$ adsorbent monolith 100 that it can be readily removed from the reactor for replacement or cleaning.

As illustrated at FIGS. 7 and 8, disposed adjacent to the exhaust opening 16 of the reactor 12 is at least one sensor bank 116 for measuring the concentration of both nitrogen oxides and ozone. This sensor bank 116 will serve to alert the operator of the apparatus 10 that adequate conversion of ozone to oxygen and adsorption of nitrogen oxides has occurred at the time of exhausting the airstream 98 from the reactor 12. Additional ozone and nitrogen oxides sensor banks 118, 120 are preferably disposed throughout the reactor 12 to capture measurements of the concentration of these pollutants. Exemplary locations for the sensors are proximate entering the intake opening 14 of the reactor 12, at the corona discharge device 42 or the UV-C device 74 as well as immediately after the ozone decomposition catalyst monolith 82 and NOx adsorption monolith 100.

These concentration measurements are beneficial in alerting the operator to the proper operation of the apparatus 10 and whether maintenance, or system tuning, may be required to adjust the concentration of ozone produced by the apparatus. When an oxygen concentrator 54 is used, the data from these sensors may optionally but preferably be fed to a microprocessor, microcontroller, or a programmable logic controller 70A for adjusting as necessary, the continuously variable control or proportional control valve 71 that feeds oxygen from the oxygen concentrator 54 as illustrated at FIGS. 13A and 13B.

If the concentration of ozone in the airstream 98 exiting the apparatus is higher than the maximum concentration limit, the sensor 116, 118 relays to the microcomputer, PLC, or microcontroller 70A the measured concentration, and a pre-programmed instruction is executed by the control device 70A to reduce the magnitude of ozone produced by the ozone generator 42. Similarly, if the concentration of nitrogen oxides, whether nitrogen dioxide or any similar compound, exceeds a set maximum concentration limit as measured by the designated sensor 118, the ozone generator 42 in concert with the oxygen concentrator 54 can adjust flow rate accordingly to increase the output of the oxygen concentrator or reduce the output of the ozone generator. Other electronic components may be used in combination with those described above to ensure proper control of ozone and nitrogen oxides, such as printed circuit boards, transistors, capacitors, resistors, and diodes.

Figure 25A:
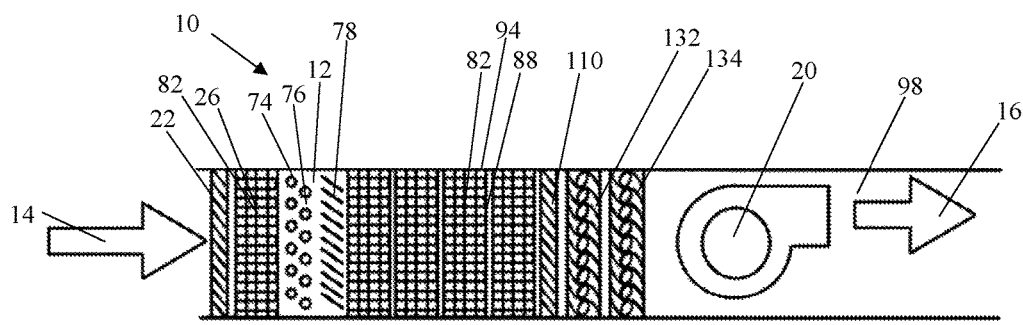
FIG. 25A is a cutaway view of an embodiment of the apparatus incorporated into an HVAC system with heating and cooling elements disposed proximate the exhaust opening.
Figure 25B:
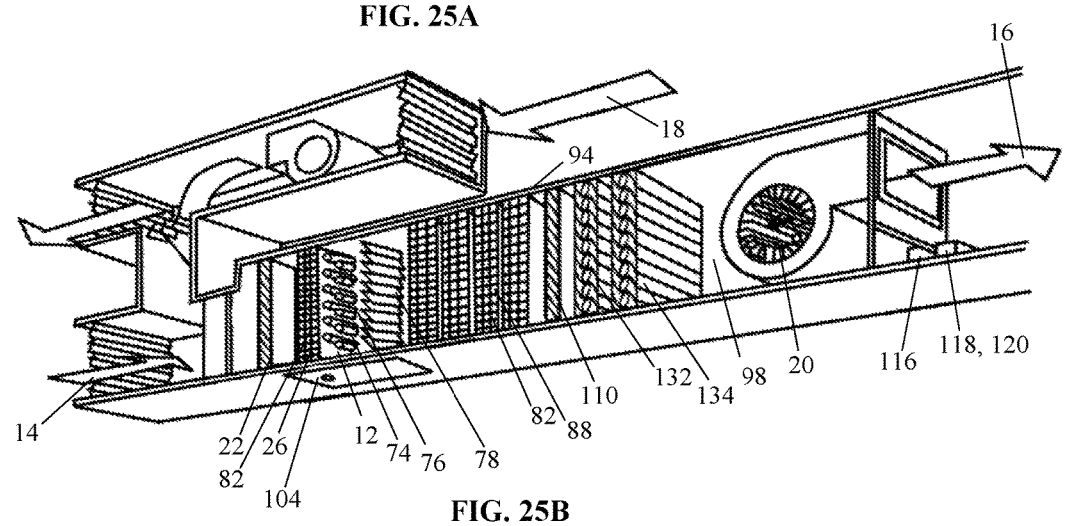
FIG. 25B is a perspective cutaway view of an embodiment of the apparatus incorporated into an HVAC system with heating and cooling elements disposed proximate the exhaust opening.

FIGS. 23A, 23B, 25A, 25B, 26A, 26B, 27A, 27B, 28 and 29 illustrate embodiments of the apparatus for integration into HVAC ducting. FIGS. 25A and 25B illustrate the apparatus 10 as integrated within a duct with heating and cooling elements 132, 134 placed proximate to the exhaust opening 16. The heating and cooling elements 132, 134 are shown to portray potential integration with the apparatus 10 disclosed herein but are not necessarily integral to the operation of the apparatus.

As illustrated in FIGS. 25A and 25B, the apparatus 10 may be integrated with heating and cooling elements 132, 134 that already exist within an HVAC system. In this way, the apparatus for HVAC ducting may be placed either before or after the existing heating and cooling elements 132, 134. The airstream 98 passes through the intake opening 14 and through the removable pre-filter 22, removing larger particles such as dust. After passing through the removable pre-filter 22, the airstream 98 flows into the UV-C ozone generator 74, where ozone 76 is generated. The ozone 76 mixes within the airstream 98, inactivating pathogens. The air and ozone mixture then passes through the baffles 78, further improving mixing and pathogen inactivation.

The airstream 98 carrying a high percentage of inactivated pathogens then flows past the ozone decomposition catalyst 82 to convert ozone 76 in the airstream to oxygen and past the $NO_x$ adsorption monolith 100. Finally, the airstream 98 passes through the exhaust filter 110, around the heating and cooling elements 132, 134, and out the exhaust opening 16. Ozone and nitrogen oxides sensor banks 116, 118, and 120 disposed within and around the reactor 12 monitor the concentration of ozone and nitrogen oxides leaving the apparatus to ensure the maximum concentration limits set by the U.S. EPA are not exceeded. Throughout the process, the fan 20 pulls the airstream 98 through the reactor 12 and out the exhaust opening 16. FIG. 25B illustrates a perspective view of the same process as described above.

Figure 23A:
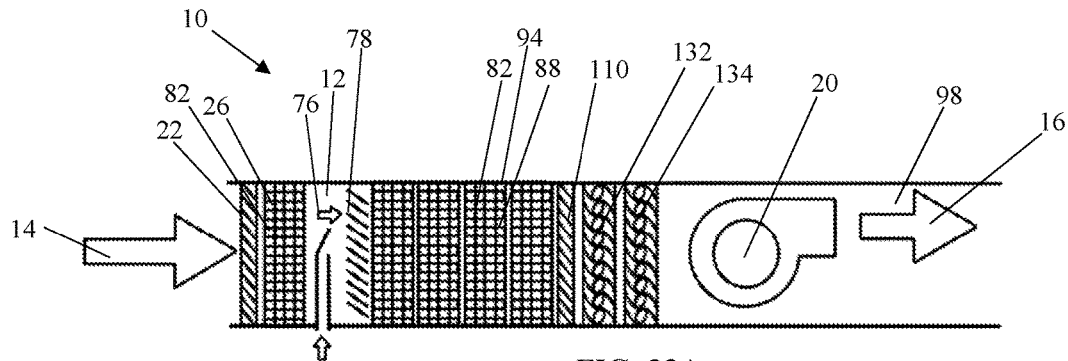
FIG. 23A is a cutaway view of an embodiment of the apparatus incorporated into an HVAC system with an external oxygen concentrator supplying a corona discharge ozone generator with injection site for releasing ozone into the reactor.
Figure 23B:
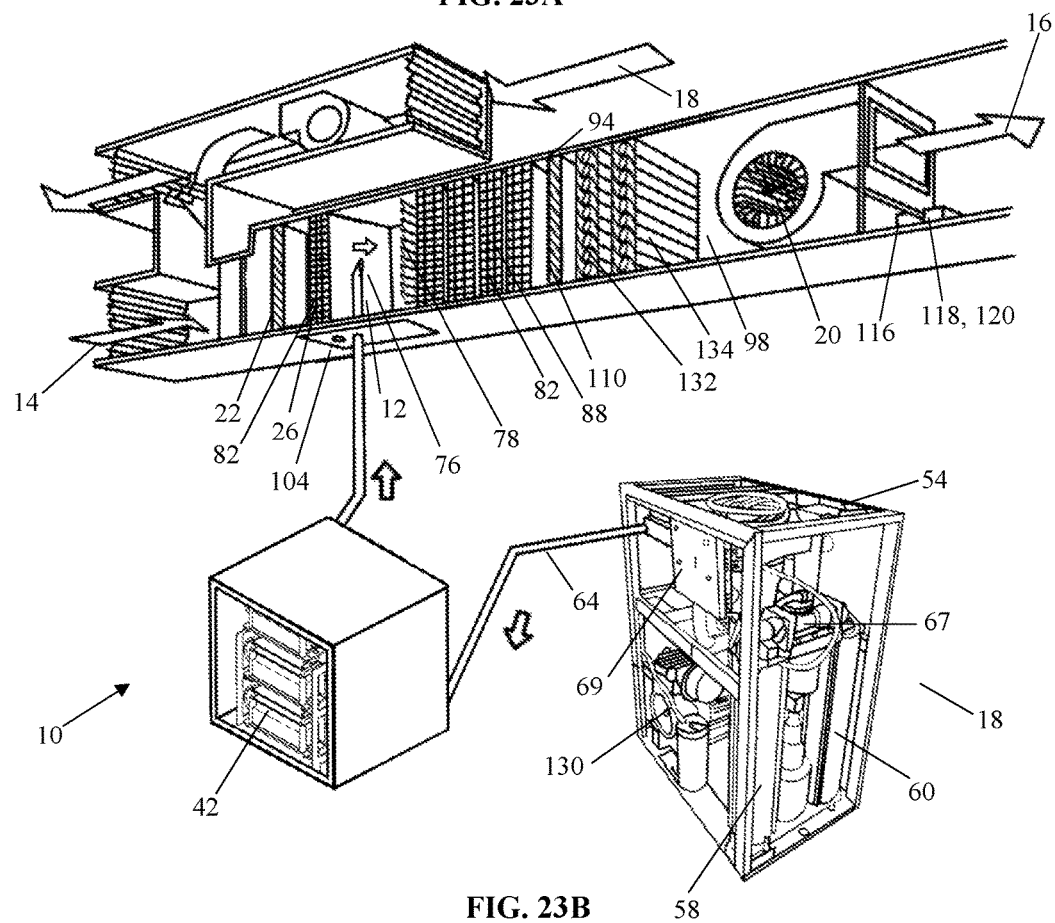
FIG. 23B is perspective cutaway view of an embodiment of the apparatus incorporated into and HVAC system with an external oxygen concentrator supplying a corona discharge ozone generator through an injection site for releasing ozone into the reactor.
Figure 24:
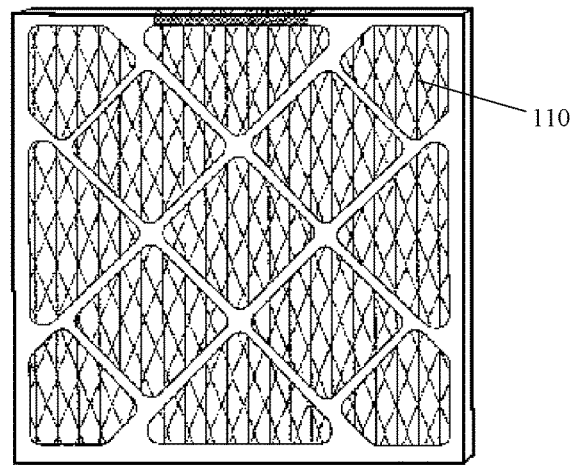
FIG. 24 is an elevation view of an embodiment of a filter located in the exhaust region of the apparatus.
Figure 26A:
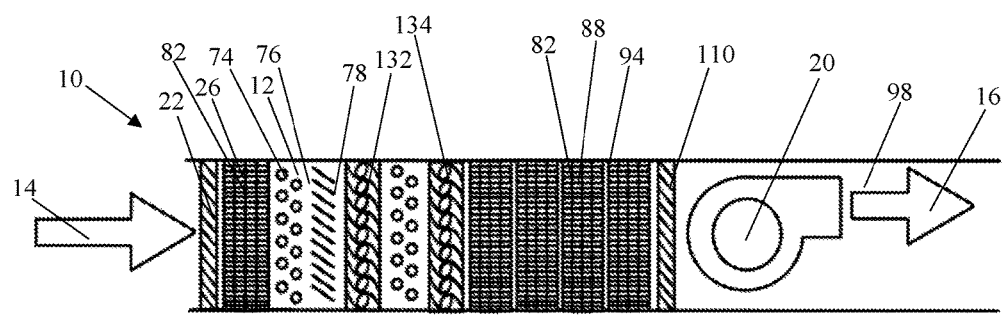
FIG. 26A is a cutaway view of an embodiment of the apparatus incorporated into an HVAC system with heating and cooling elements disposed within the reactor.
Figure 26B:
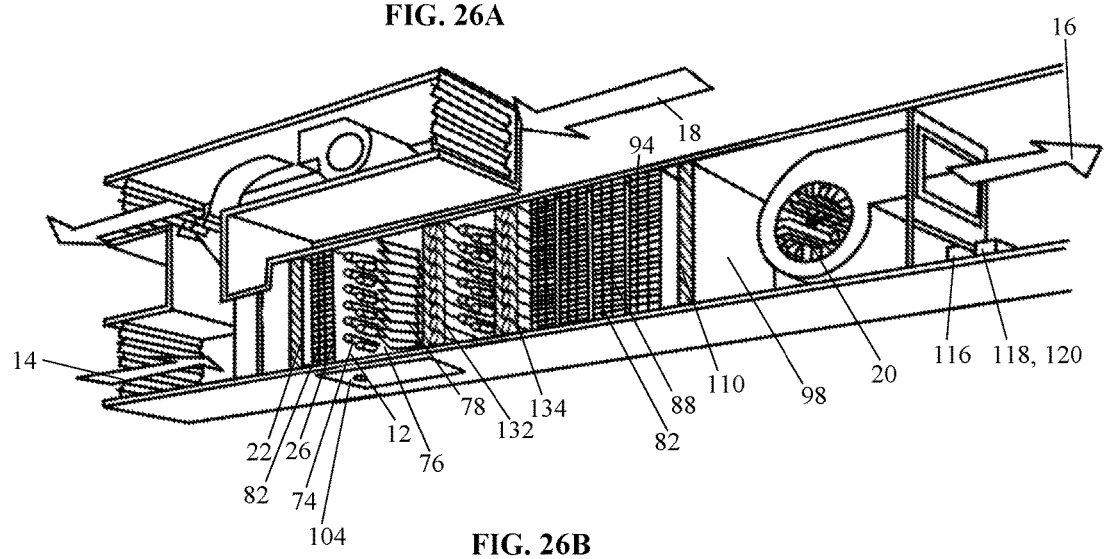
FIG. 26B is a perspective cutaway view of an embodiment of the apparatus incorporated into an HVAC system with heating and cooling elements disposed within the reactor.
Figure 27A:
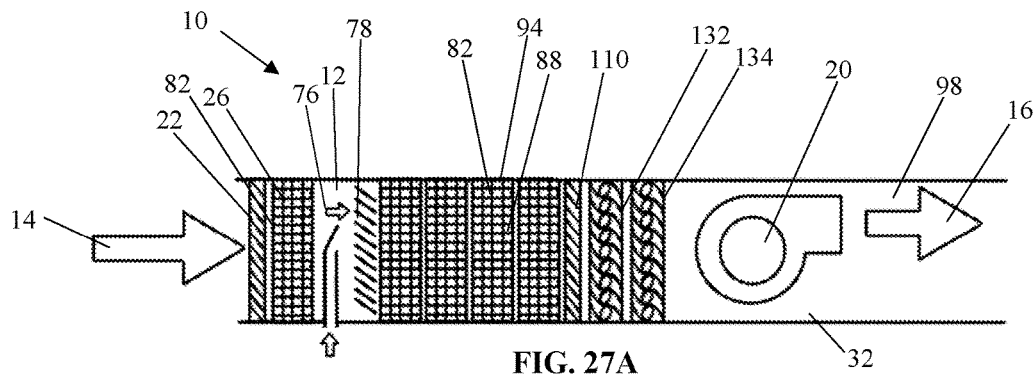
FIG. 27A is a cutaway view of an embodiment of the apparatus incorporated into and HVAC system with an external oxygen concentrator supplying a UV-C ozone generator with injection site for releasing ozone into the reactor.
Figure 27B:
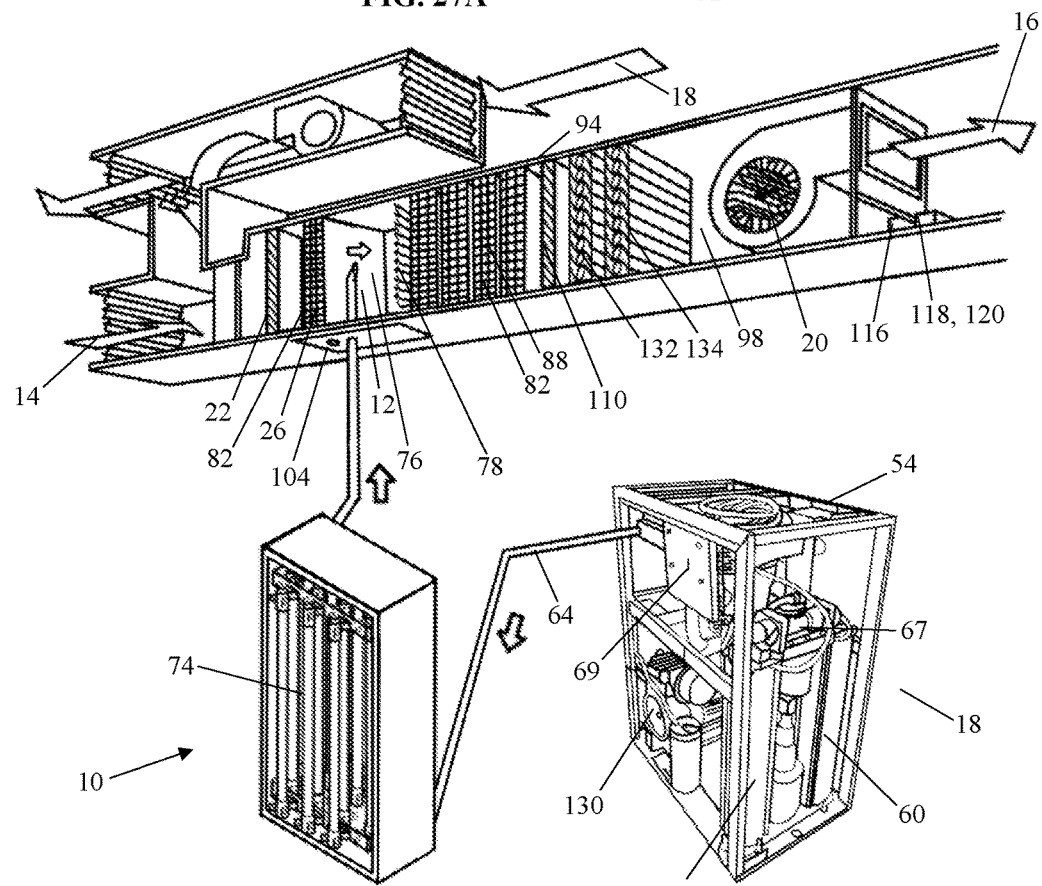
FIG. 27B is perspective cutaway view of an embodiment of the apparatus incorporated into and HVAC system with an external oxygen concentrator supplying a UV-C ozone generator with injection site for releasing ozone into the reactor.

In an alternative configuration for integration in HVAC ducting, the heating 132 and cooling 134 elements may also be placed within the reactor 12, as opposed to after the reactor 12. FIGS. 26A and 26B illustrate a side elevation and a perspective view of the apparatus 10, with heating 132 and cooling 134 elements moved from after the ozone decomposition catalyst 82 to closer to the reactor intake opening 14. In a further embodiment, FIGS. 23B and 27B illustrate similar configurations to FIGS. 26A and 26B, with the apparatus integrated in HVAC duct work. In both the configurations illustrated in FIGS. 23A and 23B and 27A and 27B, an oxygen concentrator 54 is used to increase the oxygen supply for the ozone generator. FIGS. 27A and 27B illustrate the combination with a UV-C ozone generator, while FIGS. 23A and 23B shows the combination with a corona discharge ozone generator. In each configuration, the airstream 98 enters the reactor proximate to the intake 14.

The reactor 12 contains an inlet pipe or tubing for injection of ozone 76 from the oxygen concentrator 54 fed corona discharge 42 or UV-C ozone generator 74. The oxygen concentrator releases a highly concentrated stream of oxygen into the space surrounding the corona discharge generator 42 or UV-C ozone generator 74, limiting the production of $NO_x$ compounds and increasing the production of ozone. Once the ozone 76 is injected into the airstream, the airstream passes over the baffles which increase mixing and improves pathogen inactivation, until moving to the ozone decomposition catalyst which removes the ozone.

Figure 28:
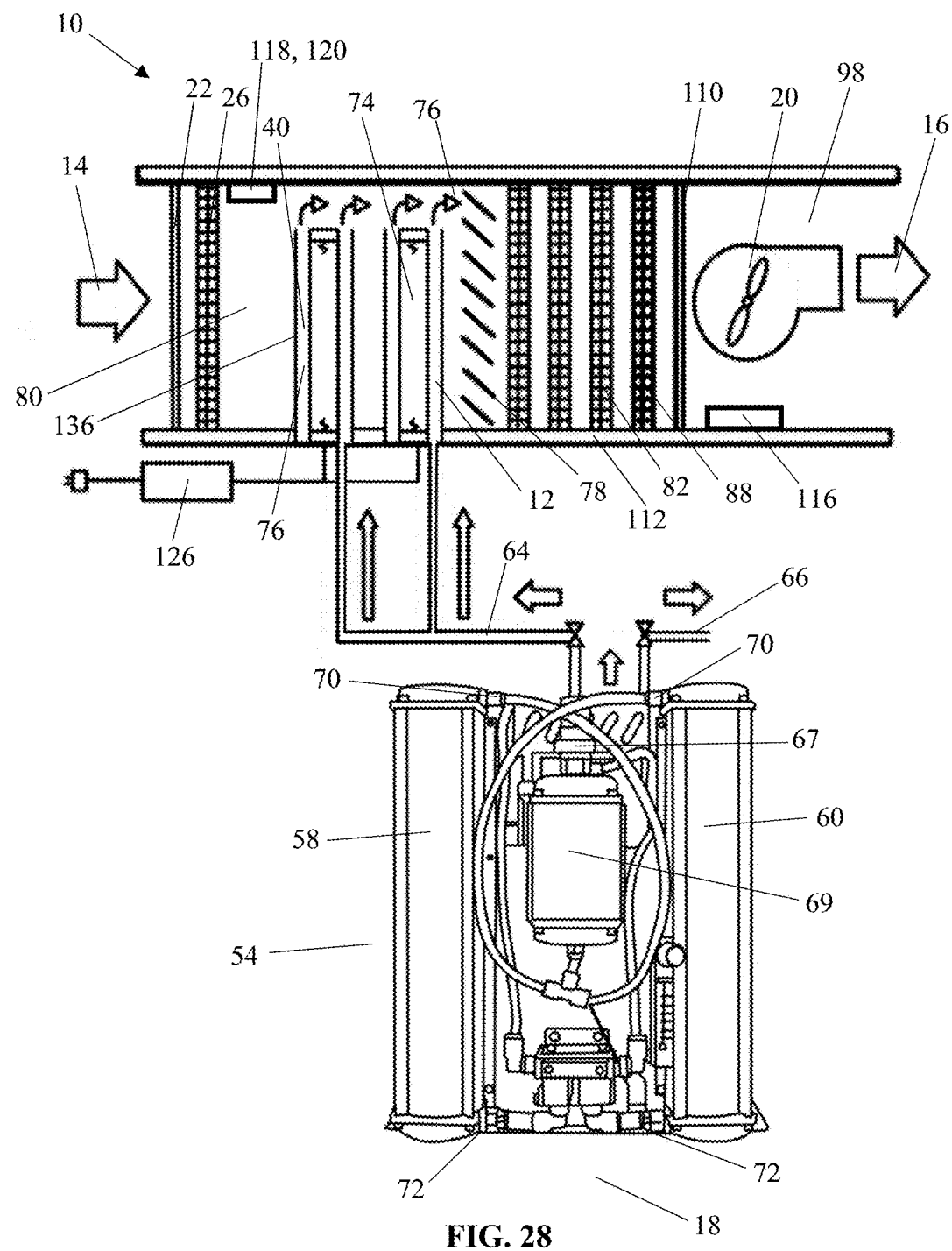
FIG. 28 is a cutaway view of an embodiment of the apparatus incorporated into an HVAC system with a transparent sleeve surrounding the UV-C ozone generator.

As shown in FIG. 28, in an alternate embodiment of the same configuration as described in FIGS. 27A and 27B, the oxygen concentrator 54 injects a concentrated ozone stream into the reactor zone 12, with the UV-C ozone generator contained within the reactor 12 as opposed to outside the reactor 12. In this configuration, the UV-C ozone generator lamps 74 are mounted perpendicular to the airstream 98 flow, with a transparent sleeve in front of the UV-C ozone generator limiting contact with the airstream and the UV-C ozone generator. The concentrated oxygen 64 leaving the oxygen concentrator 54 is injected between the lamps of the UV-C ozone generator 74, creating ozone which flows out and into the airstream 98 that is rerouted around the UV-C generator.

Figure 29:
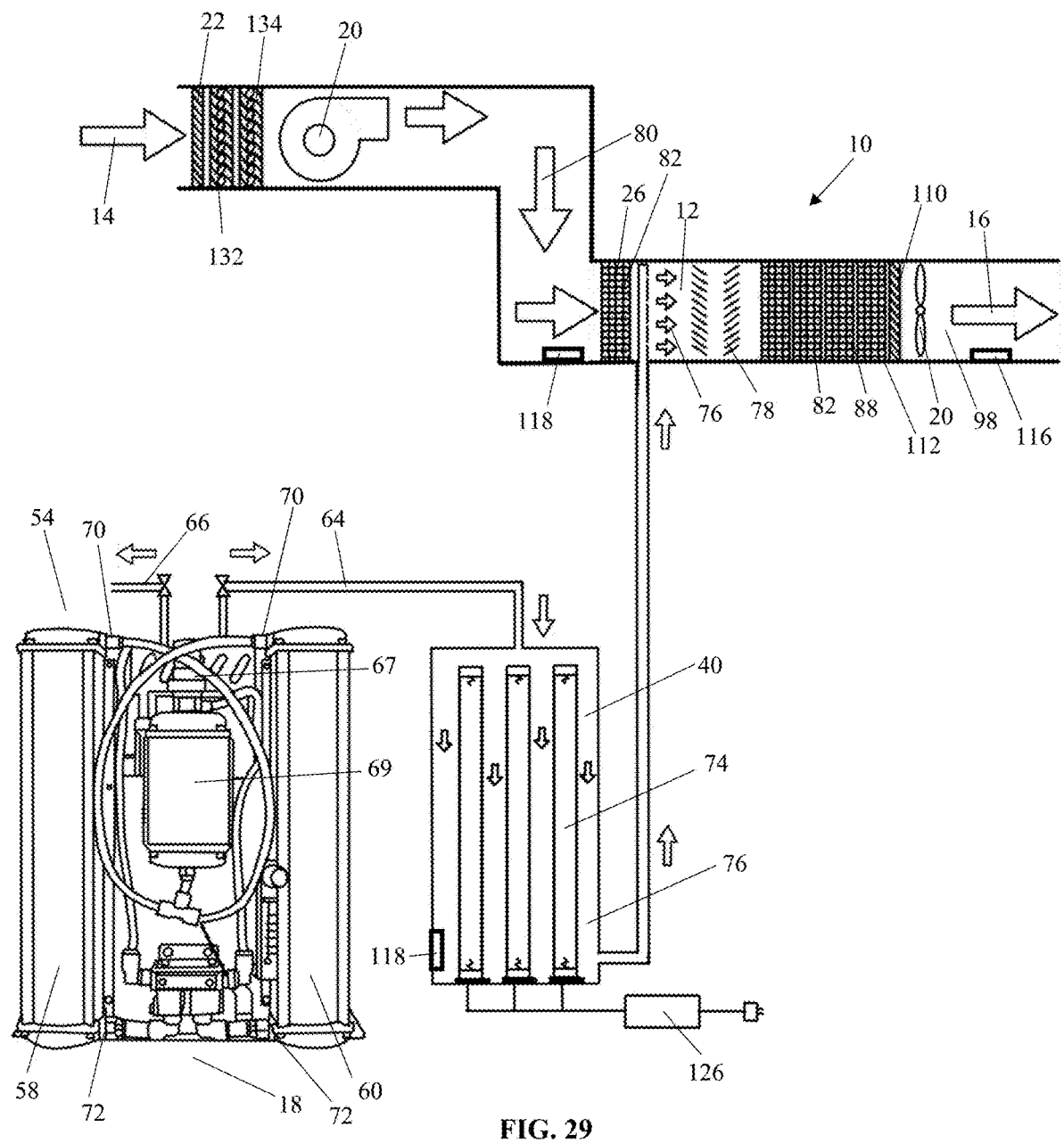
FIG. 29 is an elevated cutaway view of an embodiment of the apparatus incorporated into an HVAC system with an external oxygen concentrator supplying a UV-C ozone generator with an additional fan for reaching a desired flow rate.

In a final embodiment, the configuration as illustrated at FIG. 29 shows the same configuration as that of 27A and 27B, with the oxygen concentrator 54 and the UV-C ozone generator 74 mounted externally to the reactor 12, with ozone injected into the reactor by a pipe or tubing. In this configuration, an additional fan 20 is placed upstream of the ozone injection site to ensure the desirable flow rate is reached as the airstream travels through the reactor.

The disclosed apparatus, and systems should not be construed as limiting in any way. Instead, the present disclosure is directed toward all novel and nonobvious features and aspects of the various disclosed embodiments, alone and in various combinations and sub-combinations with one another. The disclosed apparatus and systems are not limited to any specific aspect or feature or combination thereof, nor do the disclosed embodiments require that any one or more specific advantages be present or problems be solved.

In view of the many possible embodiments to which the principles of the disclosed invention may be applied, it should be recognized that the illustrated embodiments are only examples of the disclosure and should not be taken as limiting the scope of the invention. Rather, the scope of the invention is defined by the following claims. We therefore claim as our invention all that comes within the scope of these claims.

The disclosure presented herein is believed to encompass at least one distinct invention with independent utility. While the at least one invention has been disclosed in exemplary forms, the specific embodiments thereof as described and illustrated herein are not to be considered in a limiting sense, as numerous variations are possible. Equivalent changes, modifications, and variations of the variety of embodiments, materials, compositions, and methods may be made within the scope of the present disclosure, achieving substantially similar results. The subject matter of the at least one invention includes all novel and non-obvious combinations and sub-combinations of the various elements, features, functions and/or properties disclosed herein and their equivalents.

Benefits, other advantages, and solutions to problems have been described herein regarding specific embodiments. However, the benefits, advantages, solutions to problems, and any element or combination of elements that may cause any benefits, advantage, or solution to occur or become more pronounced are not to be considered as critical, required, or essential features or elements of any or all the claims of at least one invention.

Many changes and modifications within the scope of the instant disclosure may be made without departing from the spirit thereof, and the one or more inventions described herein include all such modifications. Corresponding structures, materials, acts, and equivalents of all elements in the claims are intended to include any structure, material, or acts for performing the functions in combination with other claim elements as specifically recited. The scope of the one or more inventions should be determined by the appended claims and their legal equivalents, rather than by the examples set forth herein.

Benefits, other advantages, and solutions to problems have been described herein regarding specific embodiments. Furthermore, the connecting lines, if any, shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions.

The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

In the detailed description herein, references to "one embodiment," "an embodiment," "an example embodiment," etc., indicate that the embodiment described may include a feature, structure, or characteristic, but every embodiment may not necessarily include the feature, structure, or characteristic. Moreover, such phrases are not necessarily referring to the same embodiment. Further, when a feature, structure, or characteristic is described relating to an embodiment, it is submitted that it is within the knowledge of one skilled in the art to affect such feature, structure, or characteristic relating to other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. An apparatus for inactivation of pathogens suspended in the air, the apparatus comprising:
   a reactor space with an intake opening and an exhaust opening and an airflow path disposed between the intake and exhaust openings for air to continuously transit throughout the reactor space;
   a pre-filter for removing particulates suspended in the air transiting through the reactor space;
   a fan for propelling air through the reactor space;
   an ozone generator;
   a plurality of baffles within the reactor space proximate the ozone generator to impart turbulence to the air transiting between the intake and the exhaust openings of the reactor space;
   a catalyst disposed within the path of the airflow, after the fan to convert ozone into oxygen;
   a filter disposed in the airflow path to capture suspended particulates and pathogens prior to discharge at the exhaust opening; and at least one sensor for measuring ozone concentration within the air at the exhaust opening.

2. The apparatus of claim 1, wherein at least one of the following is disposed within the reactor space after the pre-filter (i) an ozone backflow preventer, the backflow preventer comprising a flapper valve, or (ii) a catalyst to convert ozone into oxygen.

3. The apparatus of claim 1, wherein the ozone generator comprises a corona discharge unit further comprising a heat sink to cool the corona discharge unit.

4. The apparatus of claim 1, wherein the plurality of baffles partially obstructs the airflow path within the reactor space.

5. The apparatus of claim 1, wherein the catalyst consists of manganese dioxide ($MnO_2$).

6. The apparatus of claim 1, wherein the catalyst is configured in a honeycomb configuration with a first side and a second side and with a plurality of open channels extending between the first side and the second side.

7. The apparatus of claim 1, wherein a pressure swing adsorption unit exhausts oxygen to the ozone generator to enhance the production of ozone and to reduce the conversion of atmospheric nitrogen into nitrogen oxides within the reactor space.

8. The apparatus of claim 7, wherein a valve is operable to control the flow rate of oxygen provided by the pressure swing adsorption unit to the ozone generator.

9. The apparatus of claim 8, wherein the valve is in operable communication with the ozone sensor, a nitrogen oxides sensor and a control device to optimize the rate of flow of concentrated oxygen to the ozone generator.

10. The apparatus of claim 9, wherein the control device is at least one of (i) a micro-computer, (ii) a micro-controller, or (iii) a programmable logic controller.

11. The apparatus of claim 1, wherein a concentration of nitrogen dioxide in the air at the exhaust opening is less than 100 PPB.

12. The apparatus of claim 1, wherein an adsorbent is disposed within the path of the airflow to remove nitrogen oxides compounds from the air within the reactor space, the adsorbent is selected from the group consisting of barium oxide, potassium oxide, alkali, alkaline earth metals, activated carbons, molecular sieves, metal organic frameworks, zeolites, noble metals, soda lime (NaOH—CaO mixtures), activated alumina and combinations thereof.

13. An apparatus for inactivation of pathogens suspended in the air, the apparatus comprising:
a reactor space with an intake opening and an exhaust opening and an airflow path disposed between the intake and exhaust opening for air to continuously transit throughout the reactor space;
a pre-filter for removing particulates suspended in the airflow transiting through the reactor space;
at least one of (i) a flapper valve, or (ii) a first catalyst to restrict the discharge of ozone through the intake opening;
a fan for propelling air through the reactor space;
an ozone generator disposed proximate the intake opening, wherein the ozone generator comprises at least one of (i) a corona discharge unit, or (ii) an ultraviolet light ozone generator;
a plurality of baffles within the reactor space proximate the ozone generator to impart turbulence to the air transiting within the reactor space;
a second catalyst disposed within the path of the airflow to convert ozone into oxygen;
a filter disposed in the airflow path, after the second catalyst, to capture suspended particulates and pathogens prior to discharge at the exhaust opening; and
at least one sensor for measuring the concentration of ozone within the air at the exhaust opening.

14. The apparatus of claim 13, wherein a corona discharge unit includes a heat sink to cool the corona discharge unit and thereby improve the efficiency of ozone formation.

15. The apparatus of claim 13, wherein an adsorbent disposed within the path of the airflow to remove nitrogen oxides compounds from the air within the reactor space is selected from the group consisting of barium oxide, potassium oxide, alkali and alkaline earth metals, activated carbons, molecular sieves, metal organic frameworks, zeolites, noble metals, soda lime (NaOH—CaO mixtures), activated alumina and combinations thereof.

16. The apparatus of claim 13, wherein the at least one ozone sensor is at least two sensors, a first sensor located proximate the ozone generator and a second sensor located proximate the exhaust opening.

17. The apparatus of claim 13, wherein at least one nitrogen oxides sensor is located proximate the exhaust opening and at least one nitrogen oxides sensor is located proximate the ozone generator.

18. The apparatus of claim 13, wherein the concentration of ozone at the exhaust opening is lower than the concentration set by the national ambient air quality standards at 40 CFR § 50.19.

19. The apparatus of claim 13, wherein the concentration of nitrogen dioxide at the exhaust opening is lower than the concentration established by the national ambient air quality standards at 40 CFR § 50.11.

20. An apparatus for inactivation of pathogens suspended in the air, the apparatus comprising:
a reactor space with an intake opening and an exhaust opening and an airflow path disposed between the intake and exhaust openings for air to continuously transit throughout the reactor space;
a pre-filter for removing particulates suspended in the air transiting through the reactor space;
a fan for propelling air through the reactor space;
at least one ultraviolet light ozone generator;
at least one baffle within the reactor space proximate the ozone generator to impart turbulence to the air transiting within the reactor space;
a catalyst disposed within the path of the airflow, after the fan to convert ozone into oxygen;
a filter disposed in the airflow path, after the catalyst, to capture suspended particulates and pathogens prior to discharge at the exhaust opening.

21. The apparatus of claim 20, wherein the ozone concentration generated inside the apparatus is in the range of 1 to 55 parts per million.

22. The apparatus of claim 20, wherein at least one sensor is operable for measuring an ozone concentration within the air at the exhaust opening is less than 70 PPB.

23. The apparatus of claim 20, wherein at least one of the following is disposed within the reactor space after the pre-filter (i) an ozone backflow preventer, the backflow preventer comprising a flapper valve, or (ii) a catalyst to convert ozone into oxygen.

24. The apparatus of claim 20, wherein at least one of (i) heating elements, or (ii) cooling elements are disposed proximate the exhaust opening.

25. The apparatus of claim 20, wherein at least one of (i) heating elements, or (ii) cooling elements are disposed within the reactor proximate the ozone generator.

26. An apparatus for inactivation of pathogens suspended in the air, the apparatus comprising:
a reactor space with an intake opening and an exhaust opening and an airflow path disposed between the intake and exhaust openings for air to continuously transit throughout the reactor space;
a fan for propelling air through the reactor space;
an ozone generator disposed proximate the intake opening, the ozone generator comprising at least one of (i) a corona discharge unit or (ii) an ultraviolet light ozone generator;
a plurality of baffles within the reactor space proximate the ozone generator to impart turbulence to the air transiting within the reactor space;
a catalyst disposed within the path of the airflow after the fan to convert ozone into oxygen; and a post-filter disposed in the airflow path, after the catalyst, to capture suspended particulates and pathogens prior to discharge at the exhaust opening.

27. The apparatus of claim 26, wherein the catalyst is $MnO_2$.

28. The apparatus of claim 26, wherein the fan is disposed proximate to the exhaust opening.

29. The apparatus of claim 26, wherein the filter disposed in the airflow path proximate to the exhaust is a high-efficiency particulate air (HEPA) filter.

30. The apparatus of claim 26, wherein the ozone concentration generated inside the apparatus is in the range of 1 to 55 parts per million.

31. The apparatus of claim 26, wherein the concentration of ozone at the exhaust opening is lower than the concentration set by the national ambient air quality standards at 40 CFR § 50.19.

32. The apparatus of claim 26, wherein at least one of (i) heating elements or (ii) cooling elements are disposed proximate to the exhaust opening.

33. The apparatus of claim 26, wherein at least one of (i) heating elements or (ii) cooling elements are disposed within the reactor proximate the ozone generator.

34. An apparatus for inactivation of pathogens suspended in the air, the apparatus comprising:
- a reactor space with an intake opening and an exhaust opening and an airflow path disposed between the intake and exhaust openings for air to continuously transit throughout the reactor space;
- a first fan for propelling air through the reactor space;
- a second fan for propelling air through the reactor space to achieve a desired flow rate;
- at least one of the following is disposed within the reactor after the pre-filter (i) an air backflow preventer, (ii) a catalyst to convert ozone into oxygen;
- an ozone generator disposed external to the reactor space, the ozone generator selected from the group consisting of (i) a corona discharge unit operable with a pressure swing adsorption unit and (ii) an ultraviolet light ozone generator;
- an inlet port disposed proximate the intake opening to inject the high concentration ozone from the external ozone generator into the airflow path;
- at least one of (i) a baffle or (ii) an air straightener within the reactor space proximate the ozone generator to impart turbulence to the air transiting within the reactor space;
- a catalyst disposed within the path of the airflow to convert ozone into oxygen;
- a filter disposed in the airflow path to capture suspended particulates and pathogens prior to discharge at the exhaust opening; and
- at least one sensor for measuring ozone concentration within the air at the exhaust opening.

35. The apparatus of claim 34, wherein at least one of the following is positioned before the second fan (i) an air backflow preventer, (ii) a catalyst to convert ozone into oxygen.

36. The apparatus of claim 34, wherein at least one of the following is positioned after the second fan (i) an air backflow preventer, (ii) a catalyst to convert ozone into oxygen.

37. The apparatus of claim 34, wherein the second fan is disposed proximate the exhaust opening.

38. The apparatus of claim 34, wherein the airstream delivered to the at least one external ozone generator is concentrated by a pressure swing adsorption unit to within a range of 50% to 99% oxygen.

39. The apparatus of claim 34, wherein the ozone concentration generated inside the external ozone generator is within a range of 1,000 to 60,000 parts per million.

40. The apparatus of claim 34, wherein the ozone concentration inside the apparatus is within a range of 1 to 55 parts per million.

41. The apparatus of claim 34, wherein the concentration of ozone at the exhaust opening is lower than the concentration set by the national ambient air quality standards at 40 CFR § 50.19.

42. The apparatus of claim 34, wherein a pre-filter is disposed in the airflow path before the apparatus.

43. The apparatus of claim 34, wherein at least one of (i) heating elements or (ii) cooling elements are positioned in the airflow path before the apparatus.

* * * * *